United States Patent
Han et al.

(10) Patent No.: US 12,110,281 B2
(45) Date of Patent: Oct. 8, 2024

(54) CATECHOL DERIVATIVES OR SALT THEREOF, PROCESSES FOR PREPARING THE SAME, AND PHARMACEUTICAL COMPOSITIONS COMPRISING THE SAME

(71) Applicant: HEXAPHARMATEC CO., LTD., Ansan-si (KR)

(72) Inventors: Shin Han, Ansan-si (KR); Jae-Hyoung Lee, Ansan-si (KR)

(73) Assignee: HEXAPHARMATEC CO., LTD., Ansan-si (KR)

( * ) Notice: Subject to any disclaimer, the term of this patent is extended or adjusted under 35 U.S.C. 154(b) by 868 days.

(21) Appl. No.: 17/261,561

(22) PCT Filed: Jul. 17, 2019

(86) PCT No.: PCT/KR2019/008805
§ 371 (c)(1),
(2) Date: Jan. 19, 2021

(87) PCT Pub. No.: WO2020/017878
PCT Pub. Date: Jan. 23, 2020

(65) Prior Publication Data
US 2021/0340119 A1   Nov. 4, 2021

(30) Foreign Application Priority Data

Jul. 20, 2018 (KR) .................. 10-2018-0084536

(51) Int. Cl.
C07D 333/38 (2006.01)
A61P 1/16 (2006.01)
C07D 409/12 (2006.01)

(52) U.S. Cl.
CPC .............. *C07D 333/38* (2013.01); *A61P 1/16* (2018.01); *C07D 409/12* (2013.01)

(58) Field of Classification Search
CPC ........ C07D 333/38; C07D 409/12; A61P 1/16
See application file for complete search history.

(56) References Cited

U.S. PATENT DOCUMENTS

| 10,391,067 B2 | 8/2019 | Kwon et al. |
| 10,662,169 B2 | 5/2020 | Kim et al. |
| 2007/0105892 A1 | 5/2007 | Graupe et al. |
| 2018/0243244 A1 | 8/2018 | Kwon et al. |
| 2018/0244644 A1 | 8/2018 | Kim et al. |
| 2019/0336483 A1 | 11/2019 | Lee et al. |
| 2020/0255397 A1 | 8/2020 | Kim et al. |

FOREIGN PATENT DOCUMENTS

| CN | 104725347 A | 6/2015 |
| KR | 10-2012-0131401 A | 12/2012 |
| WO | 2011/162267 A1 | 12/2011 |

OTHER PUBLICATIONS

Kozlova et al European Journal of Medicinal Chemistry 227 (2022) 113892.*
Patani et al. Chemical Reviews, 1996, vol. 96, 3147-3176.*
Barresi et al., "Iminothioethers as Hydrogen Sulfide Donors" From the Gasotransmitter Release to the Vascular Effects, Journal of Medicinal Chemistry, 2017, vol. 60, pp. 7512-7523.

* cited by examiner

*Primary Examiner* — Kamal A Saeed
(74) *Attorney, Agent, or Firm* — Vorys, Sater, Seymour and Pease LLP; Mih Suhn Koh

(57) ABSTRACT

Provided is a novel catechol derivative or pharmaceutically acceptable salt thereof having an alkyl moiety substituted with alkylamino and/or a N-alkyl-substituted thiophene-(thio)carboxamide moiety, a process for the preparation thereof, and a pharmaceutical composition including the same.

11 Claims, 4 Drawing Sheets

CATECHOL DERIVATIVES OR SALT THEREOF, PROCESSES FOR PREPARING THE SAME, AND PHARMACEUTICAL COMPOSITIONS COMPRISING THE SAME

TECHNICAL FIELD

The present invention relates to a novel catechol derivative or pharmaceutically acceptable salt thereof, a process for the preparation thereof, and a pharmaceutical composition comprising the same. More specifically, the present invention relates to a novel catechol derivative or pharmaceutically acceptable salt thereof having an alkyl moiety substituted with alkylamino and/or a N-alkyl-substituted thiophene-(thio)carboxamide moiety, a process for the preparation thereof, and a pharmaceutical composition comprising the same. The catechol derivative or pharmaceutically acceptable salt of the present invention has an excellent autophagy-inducing activity.

BACKGROUND ART

Autophagy, which is also referred to as autophagocytosis, is the natural regulated mechanism of the cell that disassembles unnecessary or dysfunctional components. It allows the orderly degradation and recycling of cellular components. During the process of autophagy, expendable cytoplasmic constituents are isolated from the rest of the cell within a double-membraned vesicle known as an autophagosome. Then, the autophagosome fuses with an available lysosome and eventually the contents of the vesicle are degraded and recycled. Three forms of autophagy are commonly described: macroautophagy, microautophagy, and chaperone-mediated autophagy (CMA). In disease, autophagy has been seen as an adaptive response to stress, promoting survival of the cell, but in other cases it appears to promote cell death and morbidity. In the extreme case of starvation, the breakdown of cellular components promotes cellular survival by maintaining cellular energy levels.

Meanwhile, when autophagy is reduced, various diseases may be caused by accumulation of misfolded proteins and so on. For example, it has been reported that the induction of autophagy can treat neurodegenerative diseases such as Huntington's disease (HD), Parkinson's disease (PD), Alzheimer's disease (AD), prion disease, multiple sclerosis, and amyotrophic lateral sclerosis (Lou Gehrig's disease) (e.g., Korean Patent No. 10-1731908). And also, it has been reported that the induction of autophagy can treat hepatic diseases such as liver fibrosis, liver cirrhosis, hepatitis, and fatty liver disease (e.g., Korean Laid-open Publication No. 10-2017-0022790). In addition, it has been reported that the induction of autophagy can treat metabolic diseases such as diabetes, hyperlipidemia, obesity, and inflammation (e.g., Korean Laid-open Publication No. 10-2018-0007307). Besides, it has been reported that the induction of autophagy can inhibit excessive immune responses associated with sepsis (e.g., Korean Laid-open Publication No. 10-2012-0131401).

Therefore, it is expected that a material inducing autophagy can be usefully applied for preventing, ameliorating or treating various diseases associated with autophagy, such as neurodegenerative diseases, hepatic diseases, metabolic diseases, sepsis, and so on.

DETAILED DESCRIPTION OF THE INVENTION

Technical Problem

The present inventors found that a certain catechol derivative or pharmaceutically acceptable salt thereof having an alkyl moiety substituted with alkylamino and/or a N-alkyl-substituted thiophene-(thio)carboxamide moiety has an excellent autophagy-inducing activity, and therefore can be usefully applied for preventing, ameliorating or treating various diseases associated with autophagy.

Therefore, the present invention provides said catechol derivative or pharmaceutically acceptable salt thereof, a process for the preparation thereof, a pharmaceutical composition comprising the same, and a use thereof.

Technical Solution

In accordance with an aspect of the present invention, there is provided a novel catechol derivative or pharmaceutically acceptable salt thereof.

In accordance with another aspect of the present invention, there is provided a process for preparing said catechol derivative or pharmaceutically acceptable salt thereof.

In accordance with still another aspect of the present invention, there is provided a pharmaceutical composition comprising said catechol derivative or pharmaceutically acceptable salt thereof as an active ingredient.

In accordance with still another aspect of the present invention, there is provided a method for treating an autophagy-associated disease in a mammal in need thereof, comprising administering to the mammal an effective amount of said catechol derivative or pharmaceutically acceptable salt thereof.

In accordance with still another aspect of the present invention, there is provided a use of said catechol derivative or pharmaceutically acceptable salt thereof for the manufacture of a medicament for preventing, ameliorating or treating an autophagy-associated disease.

Advantageous Effects

The compound of the present invention, i.e., the catechol derivative or pharmaceutically acceptable salt thereof having an alkyl moiety substituted with alkylamino and/or a N-alkyl-substituted thiophene-(thio)carboxamide moiety, has an excellent autophagy-inducing activity. Therefore, the compound or pharmaceutically acceptable salt thereof of the present invention can be usefully applied for preventing, ameliorating or treating various diseases associated with autophagy, including neurodegenerative diseases, hepatic diseases, metabolic diseases, sepsis, and so on. Especially, the catechol derivative or pharmaceutically acceptable salt thereof according to the present invention has a molecular structure capable of permeating the blood brain barrier, i.e., an alkyl-substituted amine moiety, thereby being able to be applied for preventing, ameliorating or treating cerebral blood flow-related diseases, for example neurodegenerative diseases, such as Huntington's disease (HD), Parkinson's disease (PD), Alzheimer's disease (AD), prion disease, multiple sclerosis, Lou Gehrig's disease, and the like.

BEST MODE FOR CARRYING OUT THE INVENTION

Figure 1:
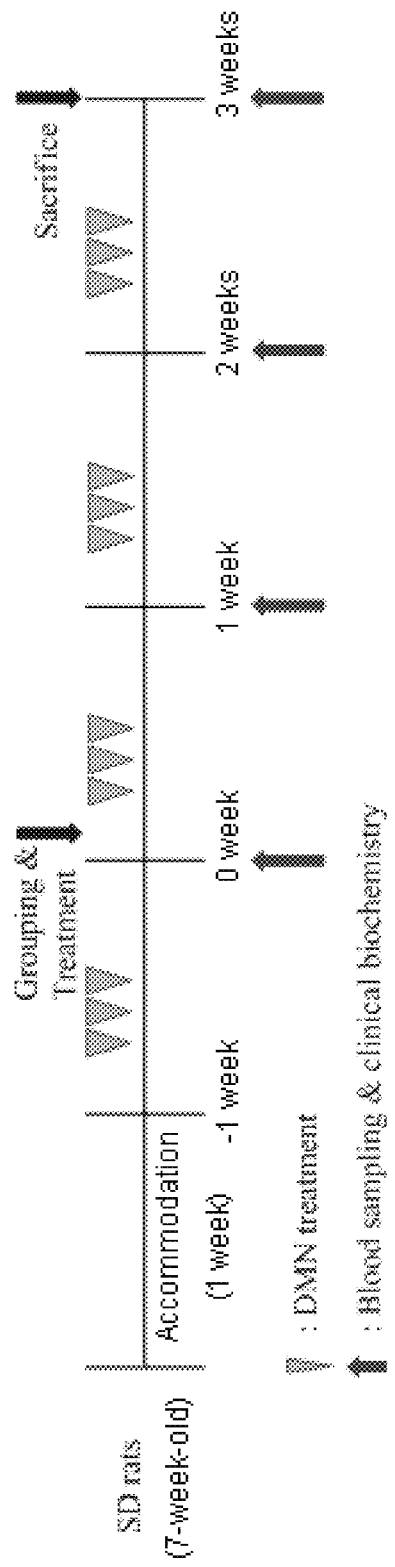
FIG. 1 shows the summarized experimental methods according to Test Example 2, in order to evaluate liver function-improving activities by oral administration in the liver injury model.

As used herein, the term "alkyl" refers to a straight or branched aliphatic hydrocarbon radical. For example, $C_1$-$C_6$ alkyl means a straight or branched aliphatic hydrocarbon having 1 to 6 carbon atoms, such as methyl, ethyl, propyl, n-butyl, n-pentyl, n-hexyl, isopropyl, isobutyl, sec-butyl, tert-butyl, neopentyl, and isopentyl.

The term "hydroxy" refers to the —OH radical. The term "alkoxy" refers to a radical formed by substituting the hydrogen atom of a hydroxy group with an alkyl. For example, $C_1$-$C_6$ alkoxy includes methoxy, ethoxy, propoxy, n-butoxy, n-pentyloxy, isopropoxy, sec-butoxy, tert-butoxy, neopentyloxy, and isopentyloxy.

The term "halogen" refers to the fluoro, bromo, chloro, or iodo radical.

The term "amino" refers to the —NH$_2$ radical. The term "alkylamino" refers to an amino formed by substituting the hydrogen atom(s) of an amino group with a mono- or di-alkyl. For example, $C_{1-6}$ alkylamino includes an amino substituted with mono- or di-$C_{1-6}$ alkyl.

The present invention provides a compound or salt thereof having an excellent autophagy-inducing activity, i.e., a compound of Formula 1 or pharmaceutically acceptable salt thereof:

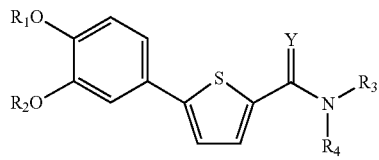

<Formula 1> wherein,
Y is O or S,
(1) when Y is O,
$R_1$ is hydrogen; or a $C_1$~$C_4$ alkyl group substituted with a mono- or di-$C_1$~$C_5$ alkylamino,
$R_2$ is a $C_1$~$C_6$ alkyl group,
$R_3$ is hydrogen, and $R_4$ is a (4-(dimethylamino)tetrahydro-2H-pyran-4-yl)methyl group; a $C_1$~$C_6$ alkyl group; a $C_1$~$C_4$ alkyl group substituted with a mono- or di-$C_1$~$C_5$ alkylamino; a $C_1$~$C_4$ alkyl group substituted with a nitrogen-containing cyclic ring (wherein the nitrogen-containing cyclic ring is optionally substituted with $C_1$~$C_4$ alkyl); or a piperidinyl group optionally substituted with $C_1$~$C_4$ alkyl, or
$R_3$ and $R_4$ are jointed each other, with the nitrogen atom to which they are attached, to form a piperazine ring (wherein the piperazine ring is optionally substituted with $C_1$~$C_4$ alkyl),
(2) when Y is S,
$R_1$ and $R_2$ are, independently of each other, hydrogen; a $C_1$~$C_6$ alkyl group; or a $C_1$~$C_4$ alkyl group substituted with a mono- or di-$C_1$~$C_5$ alkylamino, $R_3$ is hydrogen, and $R_4$ is a $C_1$~$C_6$ alkyl group; or a $C_1$~$C_4$ alkyl group substituted with a mono- or di-$C_1$~$C_5$ alkylamino, or
$R_3$ and $R_4$ are jointed each other, with the nitrogen atom to which they are attached, to form a piperazine ring (wherein the piperazine ring is optionally substituted with $C_1$~$C_4$ alkyl).

In the compound or pharmaceutically acceptable salt thereof of the present invention, Y may be O. Preferably, when Y is O, $R_1$ may be hydrogen; or a diethylaminoethyl group, and $R_2$ may be a methyl group. And also, the nitrogen-containing cyclic ring may be morpholine, piperidine, or pyrrolidine.

In an embodiment of the present invention, there is provided a compound or pharmaceutically acceptable salt thereof wherein:
Y is O,
$R_1$ is hydrogen; or a diethylaminoethyl group,
$R_2$ is a methyl group,
$R_3$ is hydrogen, and
$R_4$ is a (4-(dimethylamino)tetrahydro-2H-pyran-4-yl)methyl group; an isopropyl group; a dimethylaminoethyl group; a diethylaminoethyl group; a diisopropylaminoethyl group; a morpholinoethyl group optionally substituted with $C_1$~$C_4$ alkyl; a piperidinoethyl group optionally substituted with $C_1$~$C_4$ alkyl; a pyrrolidinoethyl group optionally substituted with $C_1$~$C_4$ alkyl; or a piperidinyl group optionally substituted with $C_1$~$C_4$ alkyl.

In another embodiment of the present invention, there is provided a compound or pharmaceutically acceptable salt thereof wherein:
Y is O,
$R_1$ is hydrogen; or a diethylaminoethyl group,
$R_2$ is a methyl group,
$R_3$ is hydrogen, and
$R_4$ is a (4-(dimethylamino)tetrahydro-2H-pyran-4-yl)methyl group.

In still another embodiment of the present invention, there is provided a compound or pharmaceutically acceptable salt thereof wherein:
Y is O,
$R_1$ is hydrogen; or a diethylaminoethyl group,
$R_2$ is a methyl group, and
$R_3$ and $R_4$ are jointed each other, with the nitrogen atom to which they are attached, to form a piperazine ring optionally substituted with $C_1$~$C_4$ alkyl.

In the compound or pharmaceutically acceptable salt thereof of the present invention, Y may be S. Preferably, when Y is S, $R_1$ may be hydrogen; or a diethylaminoethyl group, and $R_2$ is a methyl group.

In an embodiment of the present invention, there is provided a compound or pharmaceutically acceptable salt thereof wherein:
Y is S,
$R_1$ is hydrogen; or a diethylaminoethyl group,
$R_2$ is a methyl group,
$R_3$ is hydrogen, and
$R_4$ is an isopropyl group; or a diisopropylaminoethyl group.

In another embodiment of the present invention, there is provided a compound or pharmaceutically acceptable salt thereof wherein:
Y is S,
$R_1$ is hydrogen; or a diethylaminoethyl group,
$R_2$ is a methyl group, and R₃ and R₄ are jointed each other, with the nitrogen atom to which they are attached, to form a piperazine ring optionally substituted with $C_1$~$C_4$ alkyl.

Preferably, the compound or pharmaceutically acceptable salt thereof of the present invention may be one or more selected from the group consisting of:

N-(4-methylpiperazino)-5-(4-hydroxy-3-methoxyphenyl)thiophene-2-carboxamide hydrochloride;

N-(4-methylpiperazino)-5-(4-(2-diethylamino)ethoxy-3-methoxyphenyl)thiophene-2-carboxamide hydrochloride;

N-(4-methylpiperazino)-5-(4-hydroxy-3-methoxyphenyl)thiophene-2-thiocarboxamide hydrochloride;

N-(4-methylpiperazino)-5-(4-(2-diethylamino)ethoxy-3-methoxyphenyl)thiophene-2-thiocarboxamide hydrochloride;

N-(2-(diisopropylamino)ethyl)-5-(4-hydroxy-3-methoxyphenyl)thiophene-2-carboxamide hydrochloride;

N-(2-(diisopropylamino)ethyl)-5-(4-(2-diethylamino)ethoxy-3-methoxyphenyl)thiophene-2-carboxamide hydrochloride;

N-(2-(diisopropylamino)ethyl)-5-(4-hydroxy-3-methoxyphenyl)thiophene-2-thiocarboxamide hydrochloride;

N-(2-(diisopropylamino)ethyl)-5-(4-(2-diethylamino)ethoxy-3-methoxyphenyl)thiophene-2-thiocarboxamide hydrochloride;

N-isopropyl-5-(4-(2-diethylamino)ethoxy-3-methoxyphenyl)thiophene-2-carboxamide hydrochloride;

N-isopropyl-5-(4-(2-diethylamino)ethoxy-3-methoxyphenyl)thiophene-2-thiocarboxamide hydrochloride;

N-isopropyl-5-(4-hydroxy-3-methoxyphenyl)thiophene-2-thiocarboxamide;

N-(2-(diethylamino)ethyl)-5-(4-hydroxy-3-methoxyphenyl)thiophene-2-carboxamide hydrochloride;

N-(2-(diethylamino)ethyl)-5-(4-(2-diethylamino)ethoxy-3-methoxyphenyl)thiophene-2-carboxamide hydrochloride;

N-(2-(dimethylamino)ethyl)-5-(4-hydroxy-3-methoxyphenyl)thiophene-2-carboxamide hydrochloride;

N-(2-(dimethylamino)ethyl)-5-(4-(2-diethylamino)ethoxy-3-methoxyphenyl)thiophene-2-carboxamide hydrochloride;

N-(2-(4-morpholino)ethyl)-5-(4-hydroxy-3-methoxyphenyl)thiophene-2-carboxamide hydrochloride;

N-(2-(1-piperidino)ethyl)-5-(4-hydroxy-3-methoxyphenyl)thiophene-2-carboxamide hydrochloride;

N-(2-(1-piperidino)ethyl)-5-(4-(2-diethylamino)ethoxy-3-methoxyphenyl)thiophene-2-carboxamide hydrochloride;

N-(2-(1-pyrrolidino)ethyl)-5-(4-hydroxy-3-methoxyphenyl)thiophene-2-carboxamide hydrochloride;

N-((4-(dimethylamino)tetrahydro-2H-pyran-4-yl)methyl)-5-(4-hydroxy-3-methoxyphenyl)thiophene-2-carboxamide hydrochloride;

N-((4-(dimethylamino)tetrahydro-2H-pyran-4-yl)methyl)-5-(4-(2-diethylamino)ethoxy-3-methoxyphenyl)thiophene-2-carboxamide hydrochloride;

N-(4-(1-methyl)piperidinyl)-5-(4-hydroxy-3-methoxyphenyl)thiophene-2-carboxamide hydrochloride;

N-(2-(2-(1-methyl)pyrrolidino)ethyl)-5-(4-hydroxy-3-methoxyphenyl)thiophene-2-carboxamide hydrochloride;

N-(2-(2-(1-methyl)pyrrolidino)ethyl)-5-(4-(2-diethylamino)ethoxy-3-methoxyphenyl)thiophene-2-carboxamide hydrochloride;

N—((S)-2-(1-ethyl)pyrrolidinomethyl)-5-(4-hydroxy-3-methoxyphenyl)thiophene-2-carboxamide hydrochloride; and N—((S)-2-(1-ethyl)pyrrolidinomethyl)-5-(4-(2-diethylamino)ethoxy-3-methoxyphenyl)thiophene-2-carboxamide hydrochloride.

More preferably, the compound of the present invention may N-((4-(dimethylamino)tetrahydro-2H-pyran-4-yl)methyl)-5-(4-hydroxy-3-methoxyphenyl)thiophene-2-carboxamide or pharmaceutically acceptable salt thereof (for example, hydrochloride); or N-((4-(dimethylamino)tetrahydro-2H-pyran-4-yl)methyl)-5-(4-(2-diethylamino)ethoxy-3-methoxyphenyl)thiophene-2-carboxamide or pharmaceutically acceptable salt thereof (for example, hydrochloride).

The compound of Formula 1 of the present invention may be in a pharmaceutically acceptable salt form, for example in an acid addition salt form. Especially, the compound of the present invention has an alkyl-substituted amine moiety and therefore can be easily isolated in an acid addition salt form (e.g., in the form of hydrochloride), unlike the conventional compounds (e.g., the compounds disclosed in Korean Laid-open Publication No. 10-2017-0022790). That is, the compound of the present invention in the form of an acid addition salt can be easily prepared by acid/base work-up processes and be easily applied to scale-up processes, without performing column chromatography processes, unlike the conventional compounds (e.g., the compounds disclosed in Korean Laid-open Publication No. 10-2017-0022790). And also, the compound of the present invention in the form of an acid addition salt has excellent water solubility and therefore can be easily formulated and provide excellent bioavailability when it is orally administered. The acid addition salt may be derived from an inorganic acid or an organic acid, such as hydrochloric acid, hydrobromic acid, hydroiodic acid, nitric acid, sulfuric acid, phosphoric acid, acetic acid, lactic acid, citric acid, tartaric acid, succinic acid, maleic acid, malonic acid, oxalic acid, fumaric acid, gluconic acid, saccharic acid, benzoic acid, methanesulfonic acid, ethanesulfonic acid, benzenesulfonic acid, p-toluenesulfonic acid, pamoic acid, and the like, but not limited thereto. The acid addition salt may be prepared by reacting the compound of Formula 1 with an inorganic acid or an organic acid in a conventional solvent, e.g., water, alcohol, tetrahydrofuran, acetone, or a mixture thereof.

The compound of Formula 1 or pharmaceutically acceptable salt thereof may have substituent(s) containing asymmetric carbon and therefore be in the form of racemic mixture (RS) or in forms of optical isomers, such as (R) or (S) isomer. Therefore, unless otherwise indicated, the compound of Formula 1 or pharmaceutically acceptable salt thereof comprises both racemic mixture (RS) and optical isomers such as (R) or (S) isomer. And also, the compound of Formula 1 or pharmaceutically acceptable salt thereof may be in the form of cis- or trans-geometrical isomer, according to substituent(s). Therefore, unless otherwise indicated, the compound of Formula 1 or pharmaceutically acceptable salt thereof comprises both cis- and trans-geometrical isomers. And also, the compound of Formula 1 or pharmaceutically acceptable salt thereof may be in the form of one or more diastereomeric isomer(s) or a mixture thereof. Therefore, unless otherwise indicated, the compound of Formula 1 or pharmaceutically acceptable salt thereof comprises both diastereomeric isomer(s) and a mixture thereof.

The compound of formula 1 or pharmaceutically acceptable salt thereof according to the present invention may be in an anhydrous form, in a hydrate form or in a solvate form. In addition, the compound of formula 1 or pharmaceutically acceptable salt thereof according to the present invention may be in an amorphous or in a crystalline forms. Said amorphous or crystalline forms may be also in a hydrate form or in a solvate form. The hydrate or solvate may comprise water or an organic solvent in a stoichiometric or non-stoichiometric amount to the compound of formula 1 or pharmaceutically acceptable salt thereof.

The present invention also includes, within its scope, a process for preparing the compound of Formula 1 or pharmaceutically acceptable salt thereof.

For example, a compound of Formula 1 or pharmaceutically acceptable salt thereof wherein Y is O (i.e., a compound of Formula 1a or pharmaceutically acceptable salt thereof) may be prepared by acylating a compound of Formula 4 with a compound of Formula 5 to prepare a compound of Formula 2; and coupling the compound of Formula 2 with a compound of Formula 3 to prepare a compound of Formula 1a, as shown in the following Reaction Scheme 1:

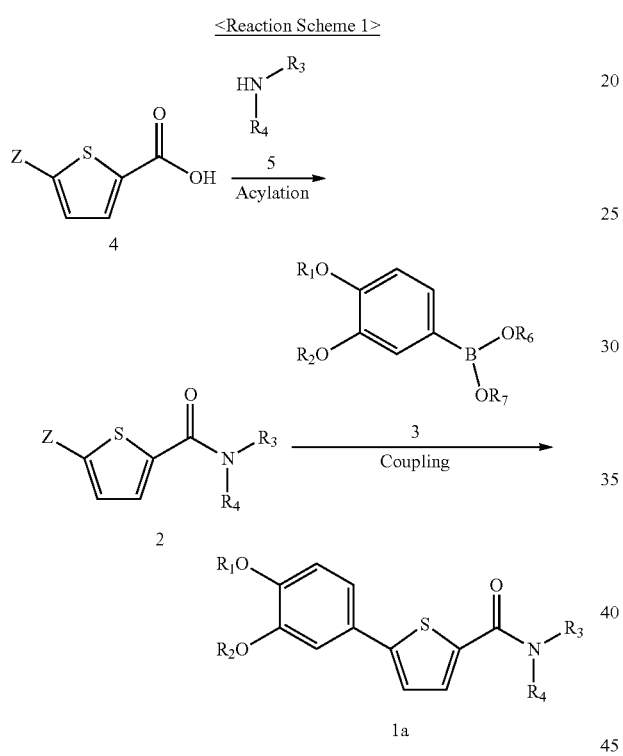

In the Reaction Scheme 1, $R_1$, $R_2$, $R_3$, and $R_4$ are the same as defined in the above, Z is halogen, and $R_6$ and $R_7$ are hydrogen; or jointed each other, with the boron atom to which they are attached, to form 4,4,5,5-tetramethyl-1,3,2-dioxaborolane.

The compounds of Formula 4 and 5, which are known compounds, are commercially available. The acylating may be carried out by using an acylating agent, such as 1-ethyl-3-(3-dimethylaminopropyl)carbodiimide (EDC), dicyclohexylcarbodiimide (DCC), 1,1'-carbonyldiimidazole (CDI), N-ethoxycarbonyl-2-ethoxy-1,2-dihydroquinoline (EEDQ). The acylating may be also carried out by reacting the compound of Formula 4 with thionyl chloride, oxalyl chloride, phosphorus chloride, and the like to prepare acyl chloride, followed by reacting the compound of Formula 5 therewith. The acylating may be carried out in a conventional organic solvent, e.g., dichloromethane.

The coupling may be carried out in the presences of a catalyst (e.g., tetrakis(triphenylphosphine)palladium(0)) and a base (e.g., sodium carbonate). The reaction between the compound of Formula 2 and the compound of Formula 3 may be carried out in a molar ratio ranging from 1:2 to 2:1, preferably in a molar ratio of about 1:1. The coupling may be carried out in water, $C_1$~$C_4$ alcohol, tetrahydrofuran, 1,2-dimethoxyethane, or a mixture thereof.

In addition, a compound of Formula 1 or pharmaceutically acceptable salt thereof wherein Y is S (i.e., a compound of Formula 1b or pharmaceutically acceptable salt thereof) may be prepared by carrying out thioamidation of a compound of Formula 2 to prepare a compound of Formula 6; and coupling the compound of Formula 6 with a compound of Formula 3 to prepare a compound of Formula 1b, as shown in the following Reaction Scheme 2:

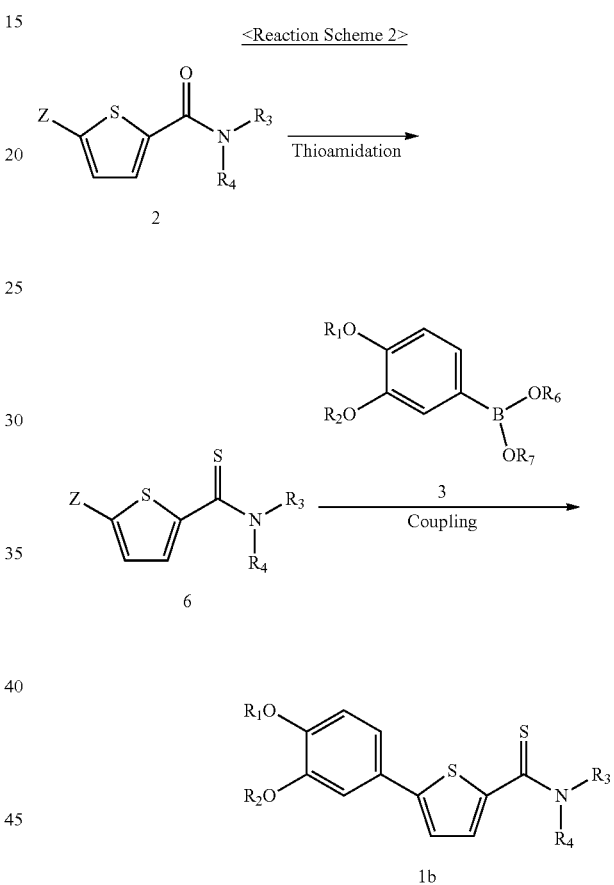

In the Reaction Scheme 2, $R_1$, $R_2$, $R_3$, $R_4$, Z, $R_6$ and $R_7$ are the same as defined in the above.

In the Reaction Scheme 2, the compound of Formula 2 may be prepared as described in Reaction Scheme 1. The thioamidation may be carried out by reacting the compound of Formula 2 with $P_4S_{10}$, bis(tricyclohexyltin) sulfide or Lawesson's reagent. The thioamidation reaction may be performed in toluene, dichloromethane, tetrahydrofuran, or a mixed solvent thereof. In addition, the coupling reaction may be carried out as described in Reaction Scheme 1, using the compound of Formula 6 instead of the compound of Formula 2.

And also, a compound of Formula 1 or pharmaceutically acceptable salt thereof wherein Y is S (i.e., a compound of Formula 1b or pharmaceutically acceptable salt thereof) may be prepared by carrying out thioamidation reaction of a compound of Formula 1a to prepare a compound of Formula 1b, as shown in the following Reaction Scheme 3:

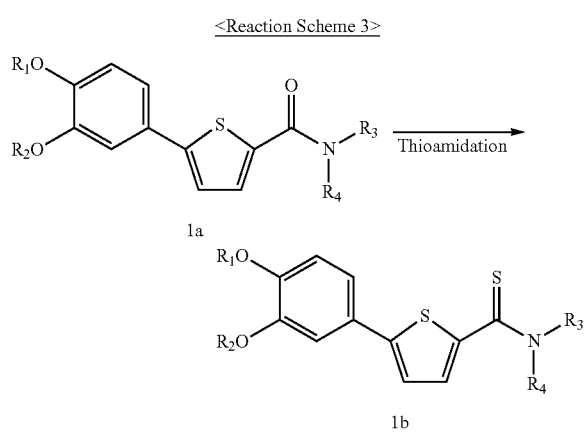

<Reaction Scheme 3>

1a

1b

In the Reaction Scheme 3, $R_1$, $R_2$, $R_3$, and $R_4$ are the same as defined in the above.

In the Reaction Scheme 3, the compound of Formula 1a may be prepared as described in Reaction Scheme 1. In addition, the thioamidation may be carried out as described in Reaction Scheme 2, using the compound of Formula 1a instead of the compound of Formula 2.

The catechol derivative of the present invention, i.e., the compound of Formula 1 or pharmaceutically acceptable salt thereof, has an excellent autophagy-inducing activity. Therefore, the compound of Formula 1 or pharmaceutically acceptable salt thereof of the present invention can be usefully applied for preventing, ameliorating or treating various diseases associated with autophagy, including neurodegenerative diseases, hepatic diseases, metabolic diseases, sepsis, and so on.

Therefore, the present invention includes, within its scope, a pharmaceutical composition for inducing autophagy, comprising a therapeutically effective amount of the compound of Formula 1 or pharmaceutically acceptable salt thereof as an active ingredient.

The diseases associated with autophagy includes, without limitation, various diseases that can be prevented, ameliorated, or treated through the induction of autophagy. For example, the pharmaceutical composition of the present invention may be a pharmaceutical composition for preventing, ameliorating or treating neurodegenerative diseases selected from the group consisting of Huntington's disease, Parkinson's disease, Alzheimer's disease, prion disease, multiple sclerosis, and Lou Gehrig's disease; hepatic diseases selected from the group consisting of liver fibrosis, liver cirrhosis, hepatitis, and fatty liver disease; metabolic diseases selected from the group consisting of diabetes, hyperlipidemia, obesity, and inflammation; or sepsis.

The pharmaceutical composition of the present invention may comprise a pharmaceutically acceptable carrier, such as diluents, disintegrants, sweeteners, lubricants, or flavoring agents. The pharmaceutical composition may be formulated to an oral dosage form such as tablets, capsules, powders, granules, suspensions, emulsions, or syrups; or a parenteral dosage form such as external solutions, external suspensions, external emulsions, gels (e.g., ointments), inhalants, sprays, injections, according to conventional methods. The dosage form may be various forms, e.g., dosage forms for single administration or for multiple administrations.

The pharmaceutical composition of the present invention may comprise, for example, a diluent (e.g., lactose, corn starch, etc); a lubricant (e.g., magnesium stearate); an emulsifying agent; a suspending agent; a stabilizer; and/or an isotonic agent. If necessary, the composition further comprises sweeteners and/or flavoring agents.

The composition of the present invention may be administered orally or parenterally, including inhalable, intravenous, intraperitoneal, subcutaneous, intracerebroventricular, rectal and topical routes of administration. Therefore, the composition of the present invention may be formulated into various forms such as tablets, capsules, aqueous solutions or suspensions. In the case of tablets for oral administration, carriers such as lactose, corn starch, and lubricating agents, e.g. magnesium stearate, are conventionally used. In the case of capsules for oral administration, lactose and/or dried corn starch can be used as a diluent. When an aqueous suspension is required for oral administration, the active ingredient may be combined with emulsifying and/or suspending agents. If desired, certain sweetening and/or flavoring agents may be used. For intramuscular, intraperitoneal, subcutaneous and intravenous administration, sterile solutions of the active ingredient are usually prepared, and the pH of the solutions should be suitably adjusted and buffered. For intravenous administration, the total concentration of solutes should be controlled in order to render the preparation isotonic. The composition of the present invention may be in the form of an aqueous solution containing pharmaceutically acceptable carriers, e.g., saline having a pH level of 7.4. The solutions may be introduced into a patient's intramuscular bloodstream by local bolus injection.

The catechol derivative of the present invention, i.e., the compound of Formula 1 or pharmaceutically acceptable salt thereof, may be administered in a therapeutically effective amount ranging from about 0.0001 mg/kg to about 100 mg/kg per day, preferably from about 0.001 mg/kg to about 100 mg/kg per day, to a subject patient. The administration may be carried out, via oral or parenteral route, once or several times a day. Of course, the dose may be changed according to the patient's age, condition, weight, susceptibility, degree of disease, route of administration, duration of administration, and the like. Depending on the method of administration, the pharmaceutical composition according to the present invention may contain the compound of Formula 1 or pharmaceutically acceptable salt thereof in an amount ranging from 0.001 to 99% by weight, preferably 0.01 to 60% by weight.

The present invention also includes, within its scope, a method for inducing autophagy in a mammal in need thereof, comprising administering to the mammal an therapeutically effective amount of the compound of Formula 1 or pharmaceutically acceptable salt thereof. For example, the present invention includes a method for preventing, ameliorating or treating neurodegenerative diseases selected from the group consisting of Huntington's disease, Parkinson's disease, Alzheimer's disease, prion disease, multiple sclerosis, and Lou Gehrig's disease; hepatic diseases selected from the group consisting of liver fibrosis, liver cirrhosis, hepatitis, and fatty liver disease; metabolic diseases selected from the group consisting of diabetes, hyperlipidemia, obesity, and inflammation; or sepsis.

The present invention also includes, within its scope, a use of the compound of Formula 1 or pharmaceutically acceptable salt thereof for the manufacture of a medicament for inducing autophagy in a mammal in need thereof. For example, the present invention includes a use of the compound of Formula 1 or pharmaceutically acceptable salt thereof for the manufacture of a medicament for preventing, ameliorating or treating neurodegenerative diseases selected from the group consisting of Huntington's disease, Parkinson's disease, Alzheimer's disease, prion disease, multiple sclerosis, and Lou Gehrig's disease; hepatic diseases selected from the group consisting of liver fibrosis, liver cirrhosis, hepatitis, and fatty liver disease; metabolic diseases selected from the group consisting of diabetes, hyperlipidemia, obesity, and inflammation; or sepsis.

The following examples and test examples are provided for illustration purposes only, and are not intended to limit the scope of the invention.

The analyses of the compounds prepared in the following Examples were carried out as follows: Nuclear magnetic resonance (NMR) spectrum analysis was carried out using Bruker 400 MHz spectrometer and chemical shifts thereof were analyzed in ppm. Column chromatography was carried out on silica gel (Merck, 70-230 mesh). Unless otherwise indicated, all starting materials were purchased commercially and used without further purification. All reactions and chromatographic fractions were analyzed by thin layer chromatography (TLC) on a 250 nm silica gel plate and visualized by ultraviolet or iodine (12) staining.

Example 1: Preparation of N-(4-methylpiperazino)-5-(4-hydroxy-3-methoxyphenyl)thiophene-2-carboxamide hydrochloride

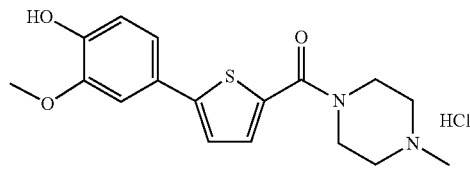

A mixture of 5-bromothiophene-2-carboxylic acid (6.21 g), dichloromethane (30 ml), and dimethylformamide (0.25 ml) was stirred for 10 minutes. Thionyl chloride (2.64 ml) was added to the mixture, which was then refluxed under stirring for 3 hours. The reaction mixture was cooled to room temperature and then concentrated under reduced pressure. Dichloromethane (45 ml) was added to the resulting concentrate, which was then cooled to 0~10° C. $K_2CO_3$ (4.62 g) was added to the reaction mixture, which was then stirred for 20 minutes. N-methylpiperazine (3.30 ml) was added to the mixture. The reaction mixture was stirred at room temperature for 2 hours and then washed with purified water (45 ml). The resulting washing water was extracted with dichloromethane (30 ml). The extract was combined with the reaction mixture. The resulting mixture was washed with purified water (30 ml), dried on anhydrous sodium sulfate, concentrated in vacuo, to obtain 8.66 g of the intermediate, i.e., N-(4-methylpiperazino)-5-bromo-thiophene-2-carboxamide. (Yield: 100%)

To N-(4-methylpiperazino)-5-bromo-thiophene-2-carboxamide (8.66 g), were added tetrakis(triphenylphosphine)palladium(0) (3.48 g) and 1,2-dimethoxyethane (51 ml). A solution of sodium carbonate (9.36 g) in purified water (51 ml) was added to the mixture, which was then stirred at room temperature for 30 minutes. A solution of (4-hydroxy-3-methoxyphenyl)-(tetramethyl-1,3-oxa)borolane (8.25 g) in ethanol (51 ml) was added to the reaction mixture, which was then stirred at about 80° C. for 5 hours. The reaction mixture was cooled to room temperature and then filtered for discarding an insoluble material. The resulting insoluble material was washed with ethanol (40 ml) and then the resulting washing solution was combined with the filtrate.

The resulting filtrate was concentrated under reduced pressure to discard the solvent. To the resulting residue, were added purified water (200 ml) and 6N hydrochloric acid (10 ml) under stirring. The resulting solution was washed with chloroform twice (100 ml and 50 ml, respectively) and then the pH thereof was adjusted to pH 8~9, using sodium hydroxide (about 3.0 g). The solution was extracted with chloroform twice (100 ml and 50 ml, respectively). The combined extract was dried on anhydrous sodium sulfate and then concentrated in vacuo. To the resulting concentrate, was added acetone (30 ml). The mixture was stirred for 1 hour and then filtered. The resulting solid was washed with acetone (5 ml), dried in vacuo at 30° C. for 3 hours to obtain N-(4-methylpiperazino)-5-(4-hydroxy-3-methoxyphenyl)thiophene-2-carboxamide (8.68 g, yield: 87.0%). The dried solid (1.50 g) was dissolved in a mixed solvent of methanol (10 ml) and chloroform (3 ml) and then 2N solution of hydrochloric acid in ethanol (1.5 ml) was added thereto. The mixture was concentrated under reduced pressure. To the resulting concentrate, was added acetone (10 ml). The mixture was stirred for 1 hour and then filtered. The resulting solid was washed with acetone (5 ml) and then dried in vacuo to obtain 1.52 g of the titled compound. (Yield: 91.6%, Overall Yield: 80.0%)

TLC $R_f$=0.20 in 10% MeOH in chloroform $^1$H NMR (400 MHz, MeOH-$d_4$) δ 7.46 (d, 1H, J=4.0 Hz), 7.31 (d, 1H, J=4.0 Hz), 7.22 (d, 1H, J=2.0 Hz), 7.16 (dd, 1H, J=2.0 Hz, 8.0 Hz), 6.98 (d, 1H, J=8.0 Hz), 4.72~4.60 (m, 2H), 3.93 (s, 3H), 3.70~3.48 (m, 4H), 3.30~3.20 (m, 2H), 2.99 (s, 3H)

Example 2: Preparation of N-(4-methylpiperazino)-5-(4-(2-diethylamino)ethoxy-3-methoxyphenyl)thiophene-2-carboxamide hydrochloride

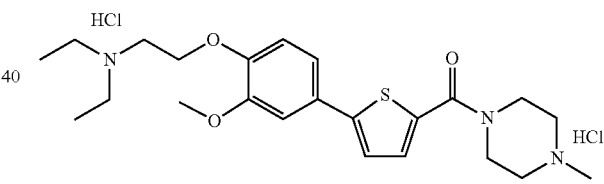

To a mixture of N-(4-methylpiperazino)-5-(4-hydroxy-3-methoxyphenyl)thiophene-2-carboxamide (3.32 g) prepared in the same procedures as in Example 1, 2-diethylaminoethyl chloride hydrochloride (1.72 g) and toluene (50 ml), was added sodium hydroxide (0.80 g). The reaction mixture was stirred at about 85° C. for 4 hours and then cooled to room temperature. Purified water (50 ml) was added to the reaction mixture, which was then stirred for 30 minutes. The separated organic layer was washed with a saturated sodium carbonate solution and then extracted with 1N hydrochloric acid (50 ml). The extract was washed with ethyl acetate (20 ml) and then the pH thereof was adjusted to pH 7~8, using sodium hydroxide (about 2.0 g). The solution was extracted with dichloromethane twice (50 ml and 30 ml, respectively). The resulting extract was dried on anhydrous sodium sulfate and then concentrated in vacuo to obtain 4.0 g of the crude product, i.e., N-(4-methylpiperazino)-5-(4-(2-diethylamino)ethoxy-3-methoxyphenyl)thiophene-2-carboxamide (Yield: 89.5%). To the resulting residue, were added 4N solution of hydrochloric acid in ethanol (6.0 ml) and acetone (60 ml). The mixture was stirred at room temperature for 1 hour and then filtered. The resulting solid was washed with acetone (5 ml) and then dried in vacuo to obtain 4.08 g of the titled compound. (Yield: 87.4%, Overall Yield: 78.2%)

TLC $R_f$=0.21 in 10% MeOH in Chloroform $^1$H NMR (400 MHz, MeOH-$d_4$) δ 7.50 (d, 1H, J=4.0 Hz), 7.41 (d, 1H, J=4.0 Hz), 7.33 (d, 1H, J=2.0 Hz), 7.30 (dd, 1H, J=2.0 Hz, 8.4 Hz), 7.13 (d, 1H, J=8.4 Hz), 4.72~4.60 (m, 2H), 4.42 (t, 2H, J=4.8 Hz), 3.97 (s, 3H), 3.70~3.60 (m, 6H), 3.50~3.38 (m, 4H), 3.30~3.20 (m, 2H), 2.99 (s, 3H), 1.42 (t, 6H, J=7.2 Hz)

Example 3: Preparation of N-(4-methylpiperazino)-5-(4-hydroxy-3-methoxyphenyl)thiophene-2-thiocarboxamide hydrochloride

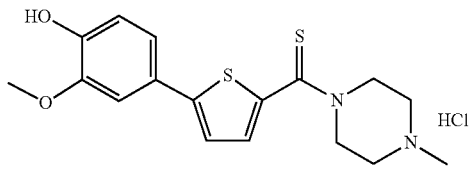

A mixture of N-(4-methylpiperazino)-5-bromo-thiophene-2-carboxamide (2.92 g) prepared in the same procedures as in Example 1, toluene (15 ml) and tetrahydrofuran (15 ml) was stirred for 10 minutes. Lawesson's reagent (4.25 g) was added to the mixture, which was then stirred at 50° C. for 5 hours. The reaction mixture was cooled to room temperature and then filtered to discard an insoluble material. Ethyl acetate (200 ml) was added to the resulting filtrate, which was then extracted with a mixed solution of purified water (200 ml) and 2N hydrochloric acid (25 ml) and a mixed solution of purified water (200 ml) and 2N hydrochloric acid (15 ml), respectively. The combined extract was washed with ethyl acetate (200 ml) and then the pH thereof was adjusted to pH 9~10, using sodium hydroxide (about 4.3 g). The solution was extracted with chloroform three times (100 ml, 50 ml and 50 ml, respectively). The resulting extract was dried on anhydrous sodium sulfate and then concentrated in vacuo to obtain 2.47 g of the intermediate, i.e., N-(4-methylpiperazino)-5-bromo-thiophene-2-thiocarboxamide. (Yield: 80.0%)

To N-(4-methylpiperazino)-5-bromo-thiophene-2-thiocarboxamide (2.47 g), were added tetrakis(triphenylphosphine)palladium(0) (1.04 g) and 1,2-dimethoxyethane (15 ml). A solution of sodium carbonate (2.81 g) in purified water (15 ml) was added to the mixture, which was then stirred at room temperature for 30 minutes. A solution of (4-hydroxy-3-methoxyphenyl)-(tetramethyl-1,3-oxa)borolane (2.48 g) in ethanol (15 ml) was added to the reaction mixture, which was then stirred at about 80° C. for 5 hours. The reaction mixture was cooled to room temperature and then filtered to discard an insoluble material. The resulting filtrate was washed with ethanol (15 ml) and then concentrated under reduced pressure to discard the solvent. To the resulting residue, were added purified water (60 ml) and 6N hydrochloric acid (3 ml) under stirring. The resulting solution was washed with chloroform twice (30 ml and 15 ml, respectively) and then the pH thereof was adjusted to pH 8~9, using sodium hydroxide (about 1.0 g). The solution was extracted with chloroform twice (30 ml and 50 ml, respectively). The resulting extract was dried on anhydrous sodium sulfate and then concentrated in vacuo. To the resulting concentrate, was added acetone (10 ml). The mixture was stirred for 1 hour and then filtered. The resulting solid (i.e., N-(4-methylpiperazino)-5-(4-hydroxy-3-methoxyphenyl)thiophene-2-thiocarboxamide) was dissolved in a mixed solvent of methanol (50 ml) and chloroform (15 ml) and then 2N solution of hydrochloric acid in ethanol (5 ml) was added thereto. The mixture was concentrated under reduced pressure. To the resulting concentrate, was added acetone (50 ml). The mixture was stirred for 1 hour and then filtered. The resulting solid was washed with acetone (5 ml) and then dried in vacuo to obtain 2.49 g of the titled compound. (Yield: 80.0%)

TLC $R_f$=0.33 in 10% MeOH in chloroform $^1$H NMR (400 MHz, MeOH-$d_4$) δ 7.30 (d, 1H, J=3.6 Hz), 7.21~7.15 (m, 3H), 6.98 (d, 1H, J=8.0 Hz), 5.20~5.10 (m, 2H), 3.93 (s, 3H), 3.85~3.65 (m, 4H), 3.32~3.25 (m, 2H), 3.00 (s, 3H)

Example 4: Preparation of N-(4-methylpiperazino)-5-(4-(2-diethylamino)ethoxy-3-methoxyphenyl)thiophene-2-thiocarboxamide hydrochloride

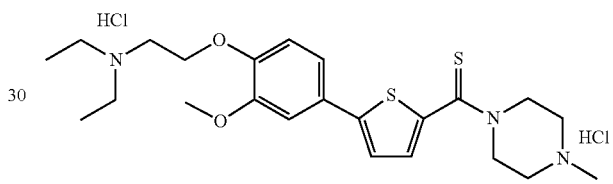

A mixture of N-(4-methylpiperazino)-5-(4-(2-diethylamino)ethoxy-3-methoxyphenyl)thiophene-2-carboxamide (4.0 g) prepared in the same procedures as in Example 2, toluene (15 ml) and tetrahydrofuran (15 ml) was stirred for 10 minutes. Lawesson's reagent (4.04 g) was added to the reaction mixture, which was then stirred at 50° C. for 5 hours. The reaction mixture was cooled to room temperature and then filtered to discard an insoluble material. Chloroform (100 ml) was added to the resulting filtrate, which was then extracted with a solution of purified water (60 ml) and 2N hydrochloric acid (40 ml). The resulting extract was washed with chloroform (30 ml) and then the pH thereof was adjusted to pH 8~9, using sodium hydroxide (about 4.4 g). The solution was extracted with chloroform three times (100 ml, 50 ml and 50 ml, respectively). The resulting extract was dried on anhydrous sodium sulfate and then concentrated in vacuo. To the resulting residue, were added a solution of 4N hydrochloric acid in ethanol (6.0 ml) and acetone (60 ml). The mixture was stirred at room temperature for 1 hour and then filtered. The resulting solid was washed with acetone (5 ml) and then dried in vacuo to obtain 4.0 g of the titled compound. (Yield: 83.0%)

TLC $R_f$=0.29 in 10% MeOH in Chloroform $^1$H NMR (400 MHz, MeOH-$d_4$) δ 7.35 (d, 1H, J=3.6 Hz), 7.32~7.26 (m, 3H), 7.12 (d, 1H, J=8.4 Hz), 5.25~5.15 (m, 2H), 4.41 (t, 2H, J=4.8 Hz), 3.97 (s, 3H), 3.85~3.75 (m, 2H), 3.66 (t, 4H, J=4.8 Hz), 3.50~3.35 (m, 6H), 3.01 (s, 3H), 1.42 (t, 3H, J=7.2 Hz)

Example 5: Preparation of N-(2-(diisopropylamino)ethyl)-5-(4-hydroxy-3-methoxyphenyl)thiophene-2-carboxamide hydrochloride

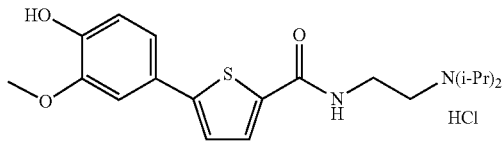

The titled compound was prepared in accordance with the same procedures as in Example 1, using 2-(diisopropylamino)ethylamine instead of N-methylpiperazine. (Yield: 80.0%)

TLC $R_f$=0.23 in 10% MeOH in chloroform $^1$H NMR (400 MHz, MeOH-d$_4$) δ 7.70 (d, 1H, J=4.0 Hz), 7.34 (d, 1H, J=4.0 Hz), 7.23 (d, 1H, J=2.0 Hz), 7.18 (dd, 1H, J=2.0 Hz, 8.0 Hz), 6.86 (d, 1H, J=8.4 Hz), 3.94 (s, 3H), 3.85 (p, 2H, J=6.4 Hz), 3.73 (t, 2H, J=6.4 Hz), 3.38 (t, 2H, J=6.4 Hz), 1.47~1.42 (m, 12H)

Example 6: Preparation of N-(2-(diisopropylamino)ethyl)-5-(4-(2-diethylamino)ethoxy-3-methoxyphenyl)thiophene-2-carboxamide hydrochloride

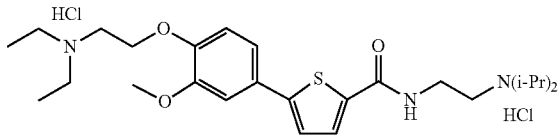

To a mixture of N-(2-(diisopropylamino)ethyl)-5-bromothiophene-2-carboxamide (4.00 g) (the intermediate prepared in the same procedures as in Example 5), tetrakis(triphenylphosphine)palladium(0) (1.39 g) and 1,2-dimethoxyethane (20 ml), was added a solution of sodium carbonate (3.80 g) in purified water (20 ml). The resulting mixture was stirred at room temperature for 30 minutes and then a solution of (4-(2-diethylamino)ethoxy-3-methoxyphenyl)-(tetramethyl-1,3-oxa)borolane (4.19 g) in ethanol (20 ml) was added thereto. The reaction mixture was stirred at about 80° C. for 5 hours, cooled to room temperature, and then filtered to discard an insoluble material. The resulting filtrate was washed with ethanol (40 ml) and then concentrated under reduced pressure to discard the solvent. To the resulting residue, was added 2N hydrochloric acid (70 ml) under stirring. The resulting solution was washed with ethyl acetate (50 ml) twice and then the pH thereof was adjusted to pH 8~9, using sodium hydroxide (about 6.0 g). The solution was extracted with dichloromethane twice (100 ml and 50 ml, respectively). The combined extract was dried on anhydrous sodium sulfate and then concentrated in vacuo. To the resulting concentrate, was added a 2N hydrochloric acid solution in ethanol (1.0 ml). The mixture was concentrated under reduced pressure. To the resulting concentrate, was added acetone (60 ml). The mixture was stirred for 1 hour and then filtered. The resulting solid was washed with acetone (5 ml) and then dried in vacuo to obtain 5.53 g of the titled compound. (Yield: 83.0%)

TLC $R_f$=0.15 in 10% MeOH in Chloroform $^1$H NMR (400 MHz, MeOH-d$_4$) δ 7.76 (d, 1H, J=4.0 Hz), 7.43 (d, 1H, J=4.0 Hz), 7.33 (d, 1H, J=2.0 Hz), 7.31 (dd, 1H, J=2.0 Hz, 8.0 Hz), 7.13 (d, 1H, J=8.0 Hz), 4.42 (t, 2H, J=4.8 Hz), 3.97 (s, 3H), 3.85 (p, 2H, J=6.4 Hz), 3.75 (t, 2H, J=6.4 Hz), 3.66 (t, 2H, J=4.8 Hz), 3.48~3.36 (m, 6H), 1.45 (dd, 12H, J=2.4 Hz, 6.4 Hz), 1.42 (t, 6H, J=7.2 Hz)

Example 7: Preparation of N-(2-(diisopropylamino)ethyl)-5-(4-hydroxy-3-methoxyphenyl)thiophene-2-thiocarboxamide hydrochloride

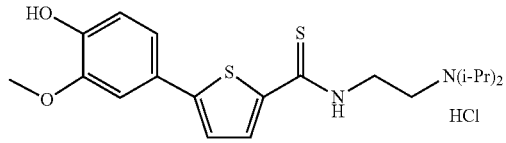

The titled compound was prepared in accordance with the same procedures as in Example 4, using N-(2-(diisopropylamino)ethyl)-5-(4-hydroxy-3-methoxyphenyl)thiophene-2-carboxamide prepared in the same procedures as in Example 5. (Yield: 75.0%)

TLC $R_f$=0.30 in 10% MeOH in Chloroform $^1$H NMR (400 MHz, MeOH-d$_4$) δ 7.58 (d, 1H, J=4.0 Hz), 7.24 (d, 1H, J=4.0 Hz), 7.18~7.08 (m, 2H), 6.76 (d, 1H, J=8.0 Hz), 4.25 (t, 2H, J=6.4 Hz), 3.81 (p, 2H, J=6.4 Hz), 3.96 (s, 3H), 3.38 (t, 2H, J=6.4 Hz), 1.45~1.38 (m, 12H)

Example 8: Preparation of N-(2-(diisopropylamino)ethyl)-5-(4-(2-diethylamino)ethoxy-3-methoxyphenyl)thiophene-2-thiocarboxamide hydrochloride

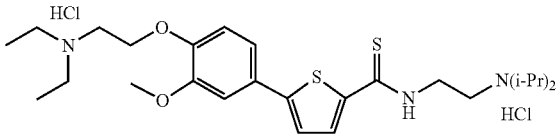

The titled compound was prepared in accordance with the same procedures as in Example 4, using N-(2-(diisopropylamino)ethyl)-5-(4-(2-diethylamino)ethoxy-3-methoxyphenyl)thiophene-2-carboxamide prepared in the same procedures as in Example 6. (Yield: 80.0%)

TLC $R_f$=0.25 in 10% MeOH in Chloroform $^1$H NMR (400 MHz, MeOH-d$_4$) δ 7.66 (d, 1H, J=4.0 Hz), 7.40 (d, 1H, J=4.0 Hz), 7.30~7.25 (m, 2H), 7.11 (d, 1H, J=8.0 Hz), 4.40 (t, 2H, J=4.8 Hz), 4.13 (t, 2H, J=6.4 Hz), 3.96 (s, 3H), 3.83 (p, 2H, J=6.4 Hz), 3.63 (t, 2H, J=4.8 Hz), 3.45~3.33 (m, 6H), 1.42 (dd, 12H, J=2.4 Hz, 6.4 Hz), 1.38 (t, 6H, J=7.2 Hz)

Example 9: Preparation of N-isopropyl-5-(4-(2-diethylamino)ethoxy-3-methoxyphenyl)thiophene-2-carboxamide hydrochloride

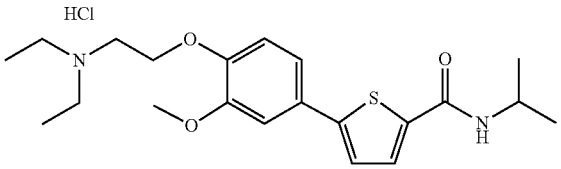 [SMILES: Cl ; CCN(CC)CCOc1ccc(-c2ccc(C(=O)NC(C)C)s2)cc1OC]

The titled compound was prepared in accordance with the same procedures as in Example 2, using isopropylamine instead of N-methylpiperazine. (Yield: 73.0%)

TLC $R_f$=0.20 in 10% MeOH in Chloroform $^1$H NMR (400 MHz, MeOH-$d_4$) δ 7.68 (d, 1H, J=4.0 Hz), 7.36 (d, 1H, J=4.0 Hz), 7.32 (d, 1H, J=2.4 Hz), 7.29 (dd, 1H, J=2.4 Hz, 8.4 Hz), 7.11 (d, 1H, J=8.4 Hz), 4.40 (t, 2H, J=4.8 Hz), 4.20 (p, 1H, J=6.8 Hz), 3.97 (s, 3H), 3.65 (t, 2H, J=4.8 Hz), 3.46~3.37 (m, 4H), 1.41 (t, 6H, J=7.2 Hz), 1.28 (d, 6H, J=6.8 Hz)

Example 10: Preparation of N-isopropyl-5-(4-(2-diethylamino)ethoxy-3-methoxyphenyl)thiophene-2-thiocarboxamide hydrochloride

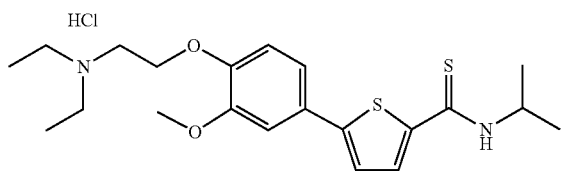 [SMILES: Cl ; CCN(CC)CCOc1ccc(-c2ccc(C(=S)NC(C)C)s2)cc1OC]

The titled compound was prepared in accordance with the same procedures as in Example 4, using N-isopropyl-5-(4-(2-diethylamino)ethoxy-3-methoxyphenyl)thiophene-2-carboxamide prepared in the same procedures as in Example 9. (Yield: 70.0%)

TLC $R_f$=0.26 in 10% MeOH in Chloroform $^1$H NMR (400 MHz, MeOH-$d_4$) δ 7.56 (d, 1H, J=4.0 Hz), 7.33 (d, 1H, J=4.0 Hz), 7.30~7.25 (m, 2H), 7.08 (d, 1H, J=8.0 Hz), 4.80 (p, 1H, J=6.8 Hz), 4.38 (t, 2H, J=4.8 Hz), 3.95 (s, 3H), 3.62 (t, 2H, J=4.8 Hz), 3.45~3.35 (m, 4H), 1.39 (t, 6H, J=7.2 Hz), 1.33 (d, 6H, J=6.8 Hz)

Example 11: Preparation of N-isopropyl-5-(4-hydroxy-3-methoxyphenyl)thiophene-2-thiocarboxamide

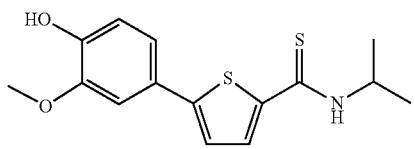 [SMILES: COc1cc(-c2ccc(C(=S)NC(C)C)s2)ccc1O]

The intermediate (i.e., N-isopropyl-5-(4-hydroxy-3-methoxyphenyl)thiophene-2-carboxamide) (3.5 g) was prepared in accordance with the same procedures as in Example 1, using isopropylamine instead of N-methylpiperazine (Yield: 85.0%). Toluene (50 ml) was added thereto and then stirred for 10 minutes. Lawesson's reagent (5.0 g) was added to the mixture, which was then stirred at about 80° C. for 5 hours. The reaction mixture was cooled to room temperature and then filtered to discard an insoluble material. The resulting filtrate was concentrated in vacuo. The resulting residue was purified with column chromatography (ethyl acetate/hexane=1/3, v/v) and then concentrated under reduced pressure. The resulting concentrate was stirred in a mixed solvent of ethyl acetate and hexane (1/3 (v/v), 10 ml) for 1 hour and then filtered. The resulting solid was washed with hexane (5 ml) and then dried at 40° C. for 5 hours to obtain 2.4 g of the titled compound. (Yield: 65.0%).

TLC $R_f$=0.35 in 10% MeOH in Chloroform $^1$H NMR (400 MHz, MeOH-$d_4$) δ 7.53 (d, 1H, J=4.0 Hz), 7.24 (d, 1H, J=4.0 Hz), 7.19 (d, 1H, J=2.0 Hz), 7.14 (dd, 1H, J=2.0 Hz, 8.4 Hz), 6.82 (d, 1H, J=8.4 Hz), 4.80 (p, 1H, J=6.8 Hz), 3.92 (s, 3H), 1.32 (d, 6H, J=6.8 Hz)

Example 12: Preparation of N-(2-(diethylamino)ethyl)-5-(4-hydroxy-3-methoxyphenyl)thiophene-2-carboxamide hydrochloride

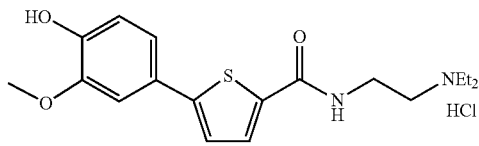

The titled compound was prepared in accordance with the same procedures as in Example 1, using 2-(diethylamino)ethylamine instead of N-methylpiperazine. (Yield: 34.8%)

TLC $R_f$=0.13 in 10% MeOH in Chloroform $^1$H NMR (400 MHz, MeOH-$d_4$) δ 7.71 (d, 1H, J=4.0 Hz), 7.32 (d, 1H, J=4.0 Hz), 7.22 (d, 1H, J=2.0 Hz), 7.17 (dd, 1H, J=2.0 Hz, 8.0 Hz), 6.86 (d, 1H, J=8.4 Hz), 3.94 (s, 3H), 3.76 (t, 2H, J=6.0 Hz), 3.41 (t, 2H, J=6.0 Hz), 3.38~3.34 (m, 4H), 1.38 (t, 6H, J=7.2 Hz)

Example 13: Preparation of N-(2-(diethylamino)ethyl)-5-(4-(2-diethylamino)ethoxy-3-methoxyphenyl)thiophene-2-carboxamide hydrochloride

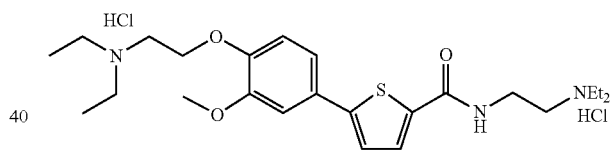

To a solution of sodium hydroxide (0.96 g) in a mixed solvent of purified water (10 ml) and tetrahydrofuran (50 ml), were added N-(2-(diethylamino)ethyl)-5-(4-hydroxy-3-methoxyphenyl)thiophene-2-carboxamide (2.21 g) prepared in the same procedures as in Example 12 and 2-diethylaminoethyl chloride hydrochloride (0.99 g). The reaction mixture was stirred at about 70° C. for 4 hours, cooled to room temperature, and then separated to a water layer and an organic layer. The obtained organic layer was concentrated under reduced pressure and then extracted with 1N hydrochloric acid (20 ml). The resulting extract was washed with ethyl acetate (20 ml) and then the pH thereof was adjusted to pH 8~9, using sodium hydroxide (about 0.9 g). The solution was extracted with dichloromethane twice (50 ml and 30 ml, respectively). The resulting extract was dried on anhydrous sodium sulfate, and then concentrated in vacuo to obtain the crude product, N-(2-(diethylamino)ethyl)-5-(4-(2-diethylamino)ethoxy-3-methoxyphenyl)thiophene-2-carboxamide. To the resulting residue, was added ethanol (15 ml). To the resulting solution, was added a solution of 1N hydrochloric acid in ether (15 ml). The mixture was heated for 1 hour and then concentrated. To the resulting residue, was added acetone (50 ml). The mixture was stirred at room temperature for 30 minutes and then filtered. The resulting solid was washed with acetone (5 ml) and then dried in vacuo to obtain 2.20 g of the titled compound. (Yield: 73.3%)

TLC $R_f$=0.23 in 20% MeOH in Chloroform $^1$H NMR (400 MHz, MeOH-d$_4$) δ 7.75 (d, 1H, J=4.0 Hz), 7.42 (d, 1H, J=4.0 Hz), 7.33 (d, 1H, J=2.0 Hz), 7.31 (dd, 1H, J=2.0 Hz, 8.0 Hz), 7.12 (d, 1H, J=8.0 Hz), 4.42 (t, 2H, J=4.8 Hz), 3.97 (s, 3H), 3.77 (t, 2H, J=6.0 Hz), 3.66 (t, 2H, J=6.0 Hz), 3.50~3.35 (m, 10H), 1.42 (t, 6H, J=7.2 Hz), 1.39 (t, 6H, J=7.2 Hz)

Example 14: Preparation of N-(2-(dimethylamino) ethyl)-5-(4-hydroxy-3-methoxyphenyl)thiophene-2-carboxamide hydrochloride

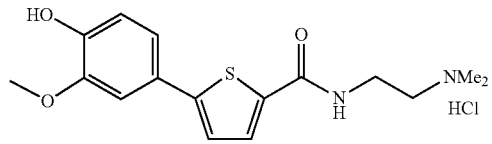 [SMILES: COc1cc(-c2ccc(C(=O)NCCN(C)C)s2)ccc1O ; Cl]

The titled compound was prepared in accordance with the same procedures as in Example 1, using 2-(dimethylamino) ethylamine instead of N-methylpiperazine. (Yield: 64.5%)

TLC $R_f$=0.12 in 10% MeOH in Chloroform $^1$H NMR (400 MHz, MeOH-d$_4$) δ 7.69 (d, 1H, J=4.0 Hz), 7.32 (d, 1H, J=4.0 Hz), 7.23 (d, 1H, J=2.0 Hz), 7.17 (dd, 1H, J=2.0 Hz, 8.0 Hz), 6.86 (d, 1H, J=8.0 Hz), 3.94 (s, 3H), 3.76 (t, 2H, J=6.0 Hz), 3.40 (t, 2H, J=6.0 Hz), 3.01 (s, 6H)

Example 15: Preparation of N-(2-(dimethylamino) ethyl)-5-(4-(2-diethylamino)ethoxy-3-methoxyphenyl)thiophene-2-carboxamide hydrochloride

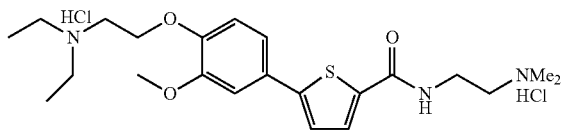 [SMILES: Cl ; CCN(CC)CCOc1ccc(-c2ccc(C(=O)NCCN(C)C)s2)cc1OC ; Cl]

The titled compound was prepared in accordance with the same procedures as in Example 13, using N-(2-(dimethylamino)ethyl)-5-(4-hydroxy-3-methoxyphenyl)thiophene-2-carboxamide prepared in the same procedures as in Example 14 instead of N-(2-(diethylamino)ethyl)-5-(4-hydroxy-3-methoxyphenyl)thiophene-2-carboxamide. (Yield: 54.7%)

TLC $R_f$=0.34 in 20% MeOH in Chloroform $^1$H NMR (400 MHz, MeOH-d$_4$) δ 7.77 (d, 1H, J=4.0 Hz), 7.41 (d, 1H, J=4.0 Hz), 7.33 (d, 1H, J=2.0 Hz), 7.30 (dd, 1H, J=2.0 Hz, 8.0 Hz), 7.12 (d, 1H, J=8.4 Hz), 4.42 (t, 2H, J=4.8 Hz), 3.97 (s, 3H), 3.78 (t, 2H, J=6.0 Hz), 3.66 (t, 2H, J=6.0 Hz), 3.50~3.35 (m, 6H), 3.01 (s, 6H), 1.42 (t, 6H, J=7.2 Hz)

Example 16: Preparation of N-(2-(4-morpholino) ethyl)-5-(4-hydroxy-3-methoxyphenyl)thiophene-2-carboxamide hydrochloride

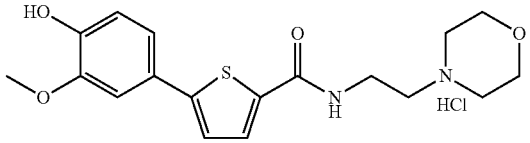 [SMILES: COc1cc(-c2ccc(C(=O)NCCN3CCOCC3)s2)ccc1O ; Cl]

The titled compound was prepared in accordance with the same procedures as in Example 1, using 4-(2-aminoethyl) morpholine instead of N-methylpiperazine. (Yield: 16.8%)

TLC $R_f$=0.32 in 10% MeOH in Chloroform $^1$H NMR (400 MHz, MeOH-d$_4$) δ 7.71 (d, 1H, J=4.0 Hz), 7.33 (d, 1H, J=4.0 Hz), 7.23 (d, 1H, J=2.0 Hz), 7.17 (dd, 1H, J=2.0 Hz, 8.0 Hz), 6.86 (d, 1H, J=8.0 Hz), 4.14~4.09 (m, 2H), 3.94 (s, 3H), 3.87~3.77 (m, 4H), 3.74~3.69 (m, 2H), 3.43 (t, 2H, J=5.6 Hz), 3.28~3.23 (m, 2H)

Example 17: Preparation of N-(2-(1-piperidino) ethyl)-5-(4-hydroxy-3-methoxyphenyl)thiophene-2-carboxamide hydrochloride

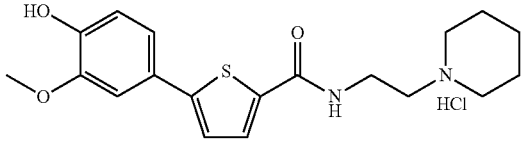 [SMILES: COc1cc(-c2ccc(C(=O)NCCN3CCCCC3)s2)ccc1O ; Cl]

The titled compound was prepared in accordance with the same procedures as in Example 1, using 1-(2-aminoethyl) piperidine instead of N-methylpiperazine. (Yield: 52.7%)

TLC $R_f$=0.15 in 10% MeOH in Chloroform $^1$H NMR (400 MHz, MeOH-d$_4$) δ 7.69 (d, 1H, J=4.0 Hz), 7.33 (d, 1H, J=4.0 Hz), 7.23 (d, 1H, J=2.0 Hz), 7.17 (dd, 1H, J=2.0 Hz, 8.0 Hz), 6.86 (d, 1H, J=8.4 Hz), 3.94 (s, 3H), 3.76 (t, 2H, J=6.0 Hz), 3.75~3.67 (m, 2H), 3.38~3.35 (m, 2H), 3.02 (t, 2H, J=12 Hz), 2.03~1.95 (m, 2H), 1.92~1.77 (m, 3H), 1.63~1.52 (m, 1H)

Example 18: Preparation of N-(2-(1-piperidino) ethyl)-5-(4-(2-diethylamino)ethoxy-3-methoxyphenyl)thiophene-2-carboxamide hydrochloride

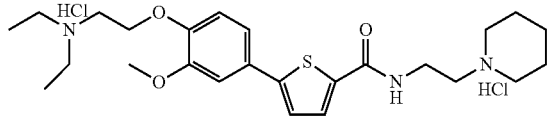 [SMILES: Cl ; CCN(CC)CCOc1ccc(-c2ccc(C(=O)NCCN3CCCCC3)s2)cc1OC ; Cl]

The titled compound was prepared in accordance with the same procedures as in Example 13, using N-(2-(1-piperidino)ethyl)-5-(4-hydroxy-3-methoxyphenyl)thiophene-2-carboxamide prepared in the same procedures as in Example 17 instead of N-(2-(diethylamino)ethyl)-5-(4-hydroxy-3-methoxyphenyl)thiophene-2-carboxamide. (Yield: 82.6%)

TLC $R_f$=0.27 in 20% MeOH in Chloroform $^1$H NMR (400 MHz, MeOH-d$_4$) δ 7.75 (d, 1H, J=4.0 Hz), 7.42 (d, 1H, J=4.0 Hz), 7.33 (d, 1H, J=2.0 Hz), 7.31 (dd, 1H, J=2.0 Hz, 8.0 Hz), 7.12 (d, 1H, J=8.4 Hz), 4.42 (t, 2H, J=4.8 Hz), 3.97 (s, 3H), 3.78 (t, 2H, J=6.0 Hz), 3.75~3.67 (m, 2H), 3.70 (t, 2H, J=11 Hz), 3.52~3.35 (m, 6H), 3.02 (m, 2H), 2.03~1.95 (m, 2H), 1.91~1.79 (m, 3H), 1.62~1.55 (m, 1H), 1.42 (t, 6H, J=7.2 Hz)

Example 19: Preparation of N-(2-(1-pyrrolidino)ethyl)-5-(4-hydroxy-3-methoxyphenyl)thiophene-2-carboxamide hydrochloride

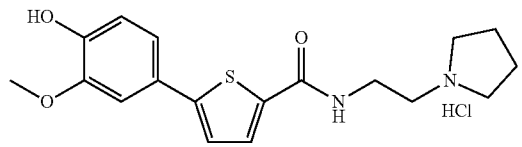 [SMILES: COc1cc(-c2ccc(C(=O)NCCN3CCCC3)s2)ccc1O ; Cl]

The titled compound was prepared in accordance with the same procedures as in Example 1, using 1-(2-aminoethyl)pyrrolidine instead of N-methylpiperazine. (Yield: 20.9%)

TLC R$_f$=0.08 in 10% MeOH in Chloroform $^1$H NMR (400 MHz, MeOH-d$_4$) δ 7.69 (d, 1H, J=4.0 Hz), 7.32 (d, 1H, J=4.0 Hz), 7.23 (d, 1H, J=2.0 Hz), 7.17 (dd, 1H, J=2.0 Hz, 8.0 Hz), 6.86 (d, 1H, J=8.0 Hz), 3.94 (s, 3H), 3.76 (t, 2H, J=6.0 Hz), 3.85~3.78 (m, 2H), 3.75 (t, 2H, J=6.0 Hz), 3.46 (t, 2H, J=6.0 Hz), 3.22~3.15 (m, 2H), 2.28~2.13 (m, 2H), 2.13~2.00 (m, 2H)

Example 20: Preparation of N-((4-(dimethylamino)tetrahydro-2H-pyran-4-yl)methyl)-5-(4-hydroxy-3-methoxyphenyl)thiophene-2-carboxamide hydrochloride

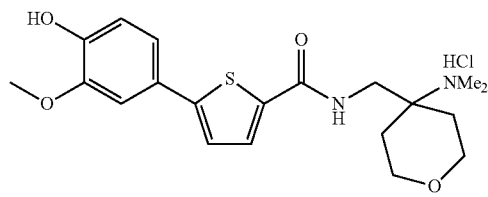 [SMILES: COc1cc(-c2ccc(C(=O)NCC3(N(C)C)CCOCC3)s2)ccc1O ; Cl]

The titled compound was prepared in accordance with the same procedures as in Example 1, using 4-(aminomethyl)-N,N-dimethyltetrahydro-2H-pyran-4-amine instead of N-methylpiperazine. (Yield: 48.4%)

TLC R$_f$=0.37 in 10% MeOH in Chloroform $^1$H NMR (400 MHz, MeOH-d$_4$) δ 7.80 (d, 1H, J=4.0 Hz), 7.34 (d, 1H, J=4.0 Hz), 7.23 (d, 1H, J=2.0 Hz), 7.18 (dd, 1H, J=2.0 Hz, 8.0 Hz), 6.86 (d, 1H, J=8.4 Hz), 4.08~4.04 (m, 2H), 4.02 (s, 2H), 3.94 (s, 3H), 3.82~3.75 (m, 2H), 2.99 (s, 6H), 2.05~1.94 (m, 4H)

Example 21: Preparation of N-((4-(dimethylamino)tetrahydro-2H-pyran-4-yl)methyl)-5-(4-(2-diethylamino)ethoxy-3-methoxyphenyl)thiophene-2-carboxamide hydrochloride

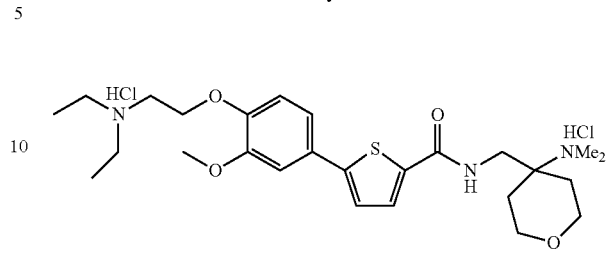

The titled compound was prepared in accordance with the same procedures as in Example 13, using N-((4-(dimethylamino)tetrahydro-2H-pyran-4-yl)methyl)-5-(4-hydroxy-3-methoxyphenyl)thiophene-2-carboxamide prepared in the same procedures as in Example 20 instead of N-(2-(diethylamino)ethyl)-5-(4-hydroxy-3-methoxyphenyl)thiophene-2-carboxamide. (Yield: 72.3%)

TLC R$_f$=0.44 in 20% MeOH in Chloroform $^1$H NMR (400 MHz, MeOH-d$_4$) δ 7.87 (d, 1H, J=4.0 Hz), 7.43 (d, 1H, J=4.0 Hz), 7.33 (d, 1H, J=2.0 Hz), 7.31 (dd, 1H, J=2.0 Hz, 8.0 Hz), 7.12 (d, 1H, J=8.4 Hz), 4.42 (t, 2H, J=4.8 Hz), 4.08~4.02 (m, 2H), 4.03 (s, 2H), 3.97 (s, 3H), 3.82~3.75 (m, 2H), 3.66 (t, 2H, J=4.8 Hz), 2.99 (s, 6H), 2.04~1.94 (m, 4H), 1.42 (t, 6H, J=7.2 Hz)

Example 22: Preparation of N-(4-(1-methyl)piperidinyl)-5-(4-hydroxy-3-methoxyphenyl)thiophene-2-carboxamide hydrochloride

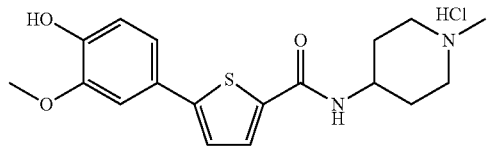

The titled compound was prepared in accordance with the same procedures as in Example 1, using 4-amino-1-methylpiperidine instead of N-methylpiperazine. (Yield: 63.4%)

TLC R$_f$=0.20 in 20% MeOH in Chloroform $^1$H NMR (400 MHz, MeOH-d$_4$) δ 7.71~7.67 (m, 1H), 7.30 (d, 1H, J=4.0 Hz), 7.22 (d, 1H, J=2.0 Hz), 7.17 (dd, 1H, J=2.0 Hz, 8.0 Hz), 6.86 (d, 1H, J=8.0 Hz), 4.18~4.08 (m, 1H), 3.94 (s, 3H), 3.62~3.57 (m, 2H), 3.25~3.14 (m, 2H), 2.92 (s, 3H), 2.31~2.24 (m, 2H), 1.98~1.87 (m, 2H)

Example 23: Preparation of N-(2-(2-(1-methyl)pyrrolidino)ethyl)-5-(4-hydroxy-3-methoxyphenyl)thiophene-2-carboxamide hydrochloride

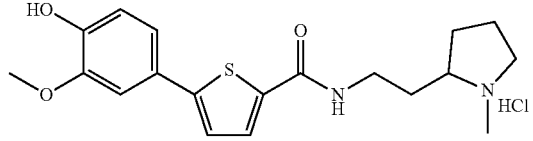 [SMILES: COc1cc(-c2ccc(C(=O)NCCC3CCCN3C)s2)ccc1O ; Cl]

The titled compound was prepared in accordance with the same procedures as in Example 1, using 2-(2-aminoethyl)-1-methyl-pyrrolidine instead of N-methylpiperazine. (Yield: 55.6%)

TLC $R_f$=0.16 in 20% MeOH in Chloroform $^1$H NMR (400 MHz, MeOH-$d_4$) δ 7.64 (d, 1H, J=4.0 Hz), 7.31 (d, 1H, J=4.0 Hz), 7.22 (d, 1H, J=2.0 Hz), 7.17 (dd, 1H, J=2.0 Hz, 8.0 Hz), 6.86 (d, 1H, J=8.0 Hz), 3.94 (s, 3H), 3.73~3.66 (m, 1H), 3.53~3.48 (m, 2H), 3.41~3.35 (m, 1H), 3.23~3.15 (m, 1H), 2.97 (s, 3H), 2.57~2.47 (m, 1H), 2.35~2.25 (m, 1H), 2.25~2.04 (m, 2H), 1.92~1.80 (m, 2H)

Example 24: Preparation of N-(2-(2-(1-methyl)pyrrolidino)ethyl)-5-(4-(2-diethylamino)ethoxy-3-methoxyphenyl)thiophene-2-carboxamide hydrochloride

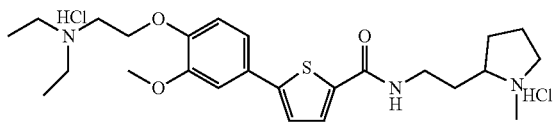 [SMILES: Cl ; CCN(CC)CCOc1ccc(-c2ccc(C(=O)NCCC3CCCN3C)s2)cc1OC ; Cl]

The titled compound was prepared in accordance with the same procedures as in Example 13, using N-(2-(2-(1-methyl)pyrrolidino)ethyl)-5-(4-hydroxy-3-methoxyphenyl)thiophene-2-carboxamide prepared in the same procedures as in Example 23 instead of N-(2-(diethylamino)ethyl)-5-(4-hydroxy-3-methoxyphenyl)thiophene-2-carboxamide. (Yield: 60.9%)

TLC $R_f$=0.12 in 20% MeOH in Chloroform $^1$H NMR (400 MHz, DMSO-$d_6$) δ 10.37 (s, 1H), 10.21 (s, 1H), 8.71 (t, 1H, J=6.0 Hz), 7.78 (d, 1H, J=4.0 Hz), 7.51 (d, 1H, J=4.0 Hz), 7.30 (d, 1H, J=2.0 Hz), 7.26 (dd, 1H, J=2.0 Hz, 8.0 Hz), 7.10 (d, 1H, J=8.0 Hz), 4.39 (t, 2H, J=4.8 Hz), 3.88 (s, 3H), 3.48~3.51 (m, 3H), 3.43~3.15 (m, 5H), 3.10~3.00 (m, 1H), 2.79 (d, 3H, J=4.8 Hz), 2.40~2.35 (m, 1H), 2.22~2.13 (m, 1H), 2.07~1.80 (m, 3H), 1.72~1.63 (m, 1H), 1.27 (t, 6H, J=7.2 Hz)

Example 25: Preparation of N—((S)-2-(1-ethyl)pyrrolidinomethyl)-5-(4-hydroxy-3-methoxyphenyl)thiophene-2-carboxamide hydrochloride

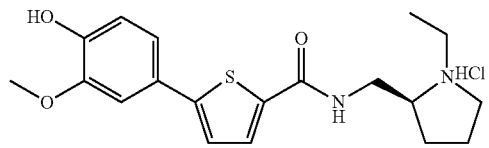 [SMILES: CCN1CCC[C@H]1CNC(=O)c1ccc(-c2ccc(O)c(OC)c2)s1 ; Cl]

The titled compound was prepared in accordance with the same procedures as in Example 1, using (S)-2-(aminomethyl)-1-ethyl-pyrrolidine instead of N-methylpiperazine. (Yield: 42.1%)

TLC $R_f$=0.29 in 20% MeOH in Chloroform $^1$H NMR (400 MHz, DMSO-$d_6$) δ 9.85 (s, 1H), 9.44 (s, 1H), 8.97 (t, 1H, J=5.6 Hz), 7.82 (d, 1H, J=4.0 Hz), 7.44 (d, 1H, J=4.0 Hz), 7.22 (d, 1H, J=2.0 Hz), 7.13 (dd, 1H, J=2.0 Hz, 8.0 Hz), 6.83 (d, 1H, J=8.0 Hz), 3.85 (s, 3H), 3.72~3.65 (m, 1H), 3.65~3.53 (m, 2H), 3.48~3.38 (m, 2H), 3.15~3.05 (m, 2H), 2.18~2.08 (m, 1H), 2.03~1.93 (m, 1H), 1.93~1.76 (m, 2H), 1.28 (t, 3H, J=7.2 Hz)

Example 26: Preparation of N—((S)-2-(1-ethyl)pyrrolidinomethyl)-5-(4-(2-diethylamino)ethoxy-3-methoxyphenyl)thiophene-2-carboxamide hydrochloride

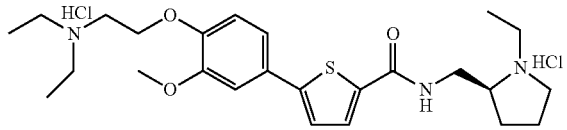 [SMILES: CCN(CC)CCOc1ccc(-c2ccc(C(=O)NC[C@@H]3CCCN3CC)s2)cc1OC ; Cl ; Cl]

The titled compound was prepared in accordance with the same procedures as in Example 13, using N—((S)-2-(1-ethyl)pyrrolidinomethyl)-5-(4-hydroxy-3-methoxyphenyl)thiophene-2-carboxamide prepared in the same procedures as in Example 25 instead of N-(2-(diethylamino)ethyl)-5-(4-hydroxy-3-methoxyphenyl)thiophene-2-carboxamide. (Yield: 37.6%)

TLC $R_f$=0.24 in 20% MeOH in Chloroform $^1$H NMR (400 MHz, DMSO-$d_6$) δ 10.41 (s, 1H), 10.25 (s, 1H), 9.14 (t, 1H, J=5.6 Hz), 7.92 (d, 1H, J=4.0 Hz), 7.53 (d, 1H, J=4.0 Hz), 7.31 (d, 1H, J=2.0 Hz), 7.27 (dd, 1H, J=2.0 Hz, 8.0 Hz), 7.11 (d, 1H, J=8.0 Hz), 4.40 (t, 2H, J=4.8 Hz), 3.88 (s, 3H), 3.82~3.72 (m, 1H), 3.67~3.50 (m, 4H), 3.48~3.40 (m, 2H), 3.40~3.18 (m, 4H), 3.18~3.03 (m, 2H), 2.18~2.08 (m, 1H), 2.03~1.93 (m, 1H), 1.93~1.75 (m, 2H), 1.45~1.35 (m, 9H)

Test Example 1: Autophagy-Inducing Activities

The autophagy-inducing activities of the compounds of the present invention were measured in Hela cells (Korean Cell Line Bank), using the Autophagy Detection Kit (ab139484, Abcam), according to the manufacturer's instructions. Specifically, 100 μL of EBSS (Earle's Balanced Salt Solution, WELGENE (LB 002-03)) containing 10% fetal bovine serum (FBS) was added to each well of a 96-well plate. Hela cells (1×10$^4$ cells) were added to each well and then incubated overnight at 37° C. in a CO$_2$ incubator so as to stabilize the cells. The medium of each well containing the stabilized cells was replaced with a medium obtained by adding 10 nM or 100 nM of the compounds prepared in Examples (test compounds) to a EBSS containing 10% FBS. As a positive control, rapamycin was dissolved in dimethyl sulfoxide and then treated at a concentration of 500 nM per well. After the treatments, the cells were incubated at 37° C. in a CO$_2$ incubator for 4 hours or 24 hours and then washed twice with the 1× assay buffer (prepared by adding 9 mL of distilled water to the 10× assay buffer). EBSS containing 5% fetal bovine serum, 1 μL/ml of Green detection reagent and 1 μL/ml of Nuclear stain was added thereto in the amount of 100 μL per well. The cells were incubated for 1 hour at 37° C. in a CO$_2$ incubator and then washed twice with the 1× assay buffer. The absorbance values were measured at 488 nm, using a microplate reader (Cytation 3). The tests were repeated four times.

The absorbance values, which were obtained by treating Hela cells with the test compounds (100 nM) and the positive control (rapamycin, 500 nM) and then incubating for 4 hours as described in above, are shown in Table 1 below. And also, the absorbance values, which were obtained by treating Hela cells with the test compounds (10 nM or 100 nM) and the positive control (rapamycin, 500 nM) and then incubating for 24 hours as described in above, are shown in Table 2 below.

TABLE 1

Absorbance (incubation for 4 hours)

| Test compounds (concentration) | Absorbance (at 488 nm) |
|---|---|
| Example 1 (100 nM) | 1321.2 |
| Example 2 (100 nM) | 1460.5 |
| Example 3 (100 nM) | 1193.8 |
| Example 4 (100 nM) | 1580.6 |
| Example 5 (100 nM) | 1348.0 |
| Example 6 (100 nM) | 1670.5 |
| Example 7 (100 nM) | 1325.5 |
| Example 8 (100 nM) | 1315.2 |
| Example 9 (100 nM) | 1320.2 |
| Example 10 (100 nM) | 1390.0 |
| Example 11 (100 nM) | 1268.4 |
| Rapamycin (500 nM) | 1306.2 |

TABLE 2

Absorbance (incubation for 24 hours)

| Test compounds | Absorbance (at 488 nm) | |
|---|---|---|
| | 10 nM | 100 nM |
| Example 1 | 1617.3 | 1660.3 |
| Example 2 | 1829.3 | 1866.3 |
| Example 3 | 1576.3 | 1754.3 |
| Example 4 | 1691.3 | 1618.3 |
| Example 5 | 1557.3 | 1618.3 |
| Example 6 | 1784.6 | 1893.7 |
| Example 7 | 1598.5 | 1605.5 |
| Example 8 | 1586.3 | 1612.3 |
| Example 9 | 1594.0 | 1951.7 |
| Example 10 | 1729.3 | 1882.3 |
| Example 11 | 1459.7 | 1731.0 |
| Rapamycin (500 nM) | 1594.2 | |

From the results in the above Table 1, it can be seen that, when incubated for 4 hours after the treatment of the test compounds, the compounds according to the present invention exhibited autophagy-inducing activities, even at 1/5 concentration, equal to or higher than that of positive control (i.e., rapamycin). Especially, from the results in Table 2, it can be seen that, when incubated for 24 hours after the treatment of the test compounds, the compounds according to the present invention exhibited superior (that is, at least five times or more) autophagy-inducing activities, even at the concentrations of 1/50 and 1/5, as compared with the positive control (i.e., rapamycin). Therefore, the compounds according to the present invention exhibit an excellent autophagy-inducing activity, thereby being able to be usefully applied for preventing, ameliorating or treating various diseases associated with autophagy, including neurodegenerative diseases, hepatic diseases, metabolic diseases, sepsis, and so on.

Test Example 2: Evaluation of Liver Function-Improving Activities by Oral Administration in the Liver Injury Model (1)

The compounds according to the present invention were orally administered to dimethylnitrosamine (DMN)-induced liver injury male SD rats for 3 weeks, so as to evaluate liver function-improving activities. Specifically, 7-week-old male SD rats (Orient Bio, Korea) were accommodated to the laboratory environment at room temperature for 7 days. General symptoms were observed and then only healthy animals were used for the experiment. The rats were divided into 9 groups (n=5 for each group), the normal control group, the group to which only DMN is administered, and the groups to which both the compound of the present invention (the compounds of Example 2, 5, 6, 9, 10, 20 or 21) and DMN are administered. DMN was dissolved in purified water and then administered intraperitoneally at the dose of 10 mg/kg for 3 consecutive weeks (3 times per week, for 4 weeks). Blood samples were collected on Day 3 after the completion of the first-week liver injury inducement and then the ALT (Alanine Transaminase) values and the AST (Aspartate Transaminase) values were measured so as to confirm the liver injury thereof. The compounds of the present invention were administered for 3 weeks, i.e., from Day 4 after the completion of the first-week liver injury inducement to the DMN-administering period. The seven compounds of the present invention were dissolved in purified water or corn oil and then orally administered, using an oral sonde, at the dose of 25 mg/kg once a day for 3 weeks. Blood samples were collected on Day 0 (3 days after the completion of the first-week liver injury inducement) and Day 7, 14 and 21 after the administration of the test compounds. The collected blood was injected into a vacutainer tube containing a clot activator and then allowed to stand at room temperature for about 20 minutes so as to coagulate each blood sample. After centrifugation for 10 minutes, the resulting serums were subjected to blood-biochemical tests. The experimental methods are summarized in FIG. 1.

The serum ALT and AST values obtained by performing the blood-biochemical test as described above are shown in Tables 3 and 4 below.

TABLE 3

| Group | ALT values (unit: U/L, average value) | | | |
|---|---|---|---|---|
| | 0 week | 1 week | 2 weeks | 3 weeks |
| Normal control group | 45.64 | 54.04 | 53.68 | 55.00 |
| DMN-administered group | 72.58 | 107.52 | 124.82 | 156.26 |
| The compound of Example 2 and DMN-administered group | 67.24 | 101.70 | 113.22 | 126.10 |
| The compound of Example 5 and DMN-administered group | 68.90 | 96.60 | 108.80 | 111.00 |
| The compound of Example 6 and DMN-administered group | 68.02 | 80.46 | 98.94 | 109.80 |
| The compound of Example 9 and DMN-administered group | 67.64 | 103.78 | 111.80 | 117.92 |
| The compound of Example 10 and DMN-administered group | 67.46 | 85.06 | 102.94 | 102.94 |
| The compound of Example 20 and DMN-administered group | 69.80 | 87.26 | 104.34 | 116.14 |
| The compound of Example 21 and DMN-administered group | 70.98 | 98.84 | 104.54 | 101.18 |

TABLE 4

| Group | AST values (unit: U/L, average value) | | | |
|---|---|---|---|---|
| | 0 week | 1 week | 2 weeks | 3 weeks |
| Normal control group | 109.64 | 142.88 | 137.60 | 142.74 |
| DMN-administered group | 140.16 | 207.10 | 250.84 | 301.04 |
| The compound of Example 2 and DMN-administered group | 143.32 | 210.86 | 223.88 | 250.76 |
| The compound of Example 5 and DMN-administered group | 137.66 | 187.26 | 219.66 | 234.22 |
| The compound of Example 6 and DMN-administered group | 141.78 | 220.86 | 215.42 | 249.56 |
| The compound of Example 9 and DMN-administered group | 140.64 | 220.58 | 241.06 | 222.50 |
| The compound of Example 10 and DMN-administered group | 145.00 | 202.52 | 218.60 | 199.34 |

TABLE 4-continued

| | AST values (unit: U/L, average value) | | | |
|---|---|---|---|---|
| Group | 0 week | 1 week | 2 weeks | 3 weeks |
| The compound of Example 20 and DMN-administered group | 136.28 | 194.88 | 209.56 | 229.74 |
| The compound of Example 21 and DMN-administered group | 142.10 | 201.30 | 208.26 | 195.10 |

As can be seen from the results of Tables 3 and 4, the serum ALT and AST values in the DMN-administered group were respectively increased about 3 times and about 2 times, after 3 weeks. However, in the groups administered with both the compounds of the present invention and DMN, the ALT values at the 3 weeks after the administration were 101.18~126.10 U/L (i.e., decreased by about 19~35% in comparison with that of the DMN-administered group); and the AST values at the 3 weeks after the administration were 195.10~250.76 U/L (i.e., decreased by about 17~35% in comparison with that of the DMN-administered group). Therefore, it can be confirmed that the compounds of the present invention have an effectively-improving activity against the liver injuries including liver fibrosis.

Test Example 3: Evaluation of Liver Function-Improving Activities by Oral Administration in the Liver Injury Model (2)

Figure 2:
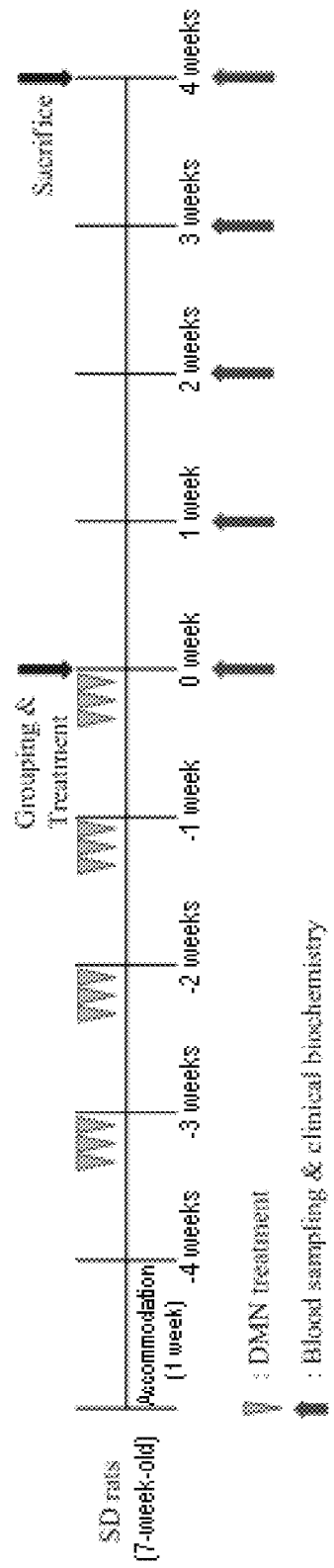
FIG. 2 shows the summarized experimental methods according to Test Example 3, in order to evaluate liver function-improving activities by oral administration in the liver injury model.

The compounds according to the present invention were orally administered to dimethylnitrosamine (DMN)-induced liver injury male SD rats for 4 weeks, so as to evaluate liver function-improving activities. Specifically, 7-week-old male SD rats (Orient Bio, Korea) were accommodated to the laboratory environment at room temperature for 7 days. General symptoms were observed and then only healthy animals were used for the experiment. The rats were divided into 3 groups (n=10 for each group), the normal control group, the group to which only DMN is administered, and the group to which both the compound of the present invention (the compound of Example 21) and DMN are administered. DMN was dissolved in purified water and then administered intraperitoneally at the dose of 10 mg/kg for 3 consecutive weeks (3 times per week, for 4 weeks). Blood samples were collected after the completion of the fourth-week liver injury inducement and then the ALT (Alanine Transaminase) values and the AST (Aspartate Transaminase) values were measured so as to confirm the liver injury thereof. The compound of the present invention was administered for 4 weeks, from Day 1 after the completion of the fourth-week liver injury inducement. The compound of the present invention (the compound of Example 21) was dissolved in purified water and then orally administered, using an oral sonde, at the dose of 25 mg/kg once a day for 4 weeks. Blood samples were collected on Day 0 (1 day after the completion of the fourth-week liver injury inducement) and Day 7, 14, 21 and 28 after the administration of the test compound. The collected blood was injected into a vacutainer tube containing a clot activator and then allowed to stand at room temperature for about 20 minutes so as to coagulate each blood sample. After centrifugation for 10 minutes, the resulting serums were subjected to blood-biochemical tests. In addition, at 24 hours after the last administration, an autopsy for hepatectomy and fixation was performed to prepare the tissue specimens thereof. After preparing the slides with the tissue specimens, hematoxylin and eosin (H&E) staining was performed thereon for microscopic observation of damages to liver tissue and inflammatory cell infiltrations in liver tissues. In addition, Masson's trichrome staining was also performed thereon for microscopic observation of collagen fiber depositions in liver tissues. The experimental methods are summarized in FIG. 2.

The serum ALT and AST values obtained by performing the blood-biochemical test as described above are shown in Tables 5 and 6 below.

TABLE 5

| | ALT values (unit: U/L, average value) | | | | |
|---|---|---|---|---|---|
| Group | 0 week | 1 week | 2 weeks | 3 weeks | 4 weeks |
| Normal control group | 50.90 | 51.15 | 50.09 | 48.38 | 48.79 |
| DMN-administered group | 254.33 | 111.02 | 64.26 | 63.65 | 65.60 |
| The compound of Example 21 and DMN-administered group | 198.02 | 92.71 | 57.61 | 44.48 | 48.33 |

TABLE 6

| | AST values (unit: U/L, average value) | | | | |
|---|---|---|---|---|---|
| Group | 0 week | 1 week | 2 weeks | 3 weeks | 4 weeks |
| Normal control group | 103.83 | 99.78 | 93.96 | 117.32 | 117.91 |
| DMN-administered group | 339.76 | 182.01 | 132.13 | 143.45 | 158.68 |
| The compound of Example 21 and DMN-administered group | 329.92 | 158.91 | 107.61 | 112.06 | 110.45 |

As can be seen from the results of Tables 5 and 6, the serum ALT and AST values in the DMN-administered group were respectively increased about 4-5 times and about 3.2 times, after 4 weeks. However, in the group administered with both the compound of the present invention (the compound of Example 21) and DMN, the ALT values at the 3 and 4 weeks after the administration were 44.48 and 48.33 U/L, respectively (i.e., decreased by 30% and 26% in comparison with that of the DMN-administered group); and the AST values at the 3 and 4 weeks after the administration were 112.06 and 110.45 U/L, respectively (i.e., decreased by 22% and 30% in comparison with that of the DMN-administered group). Therefore, it can be confirmed that the compounds of the present invention have an effectively-improving activity against the liver injuries including liver fibrosis.

In addition, the results obtained by performing hematoxylin and eosin (H&E) staining and Masson's trichrome staining as described above are shown in FIGS. 3 and 4, respectively. From the results of FIG. 3, the degrees of damages to liver tissue and the degrees of inflammatory cell infiltrations in liver tissues were measured. And also, from the results of FIG. 4, the degrees of collagen fiber depositions in liver tissues were measured. The results thereof are shown in Table 7 below.

TABLE 7

| Group | Degenerative hepatocyte numbers cells/1000 cells | Inflammatory cell numbers cells/mm$^2$ | Collagen fiber occupied regions %/mm$^2$ |
|---|---|---|---|
| Normal control group | 33.14 ± 3.23 | 40.29 ± 6.71 | 2.37 ± 0.37 |
| DMN-administered group | 559.88 ± 44.30 | 188.50 ± 9.90 | 28.68 ± 1.83 |

TABLE 7-continued

| Group | Degenerative hepatocyte numbers cells/1000 cells | Inflammatory cell numbers cells/mm$^2$ | Collagen fiber occupied regions %/mm$^2$ |
|---|---|---|---|
| The compound of Example 21 and DMN-administered group | 276.00 ± 16.64 | 85.33 ± 8.41 | 10.98 ± 1.33 |

Figure 3:
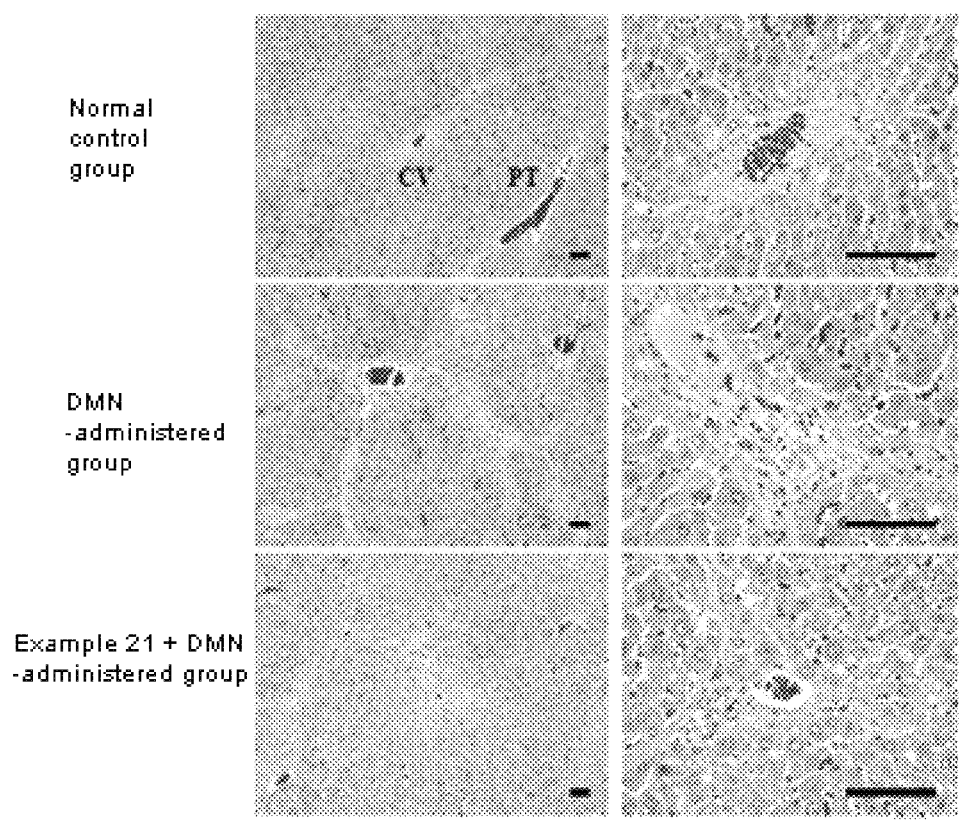
FIG. 3 show the results obtained by performing hematoxylin and eosin (H&E) staining on the tissue specimens obtained in Test Example 3. Scale bar: left black line 100 μm, right black line 100 μm.

As can be seen from the results of FIG. 3 and Table 7, the damages to liver tissue and the inflammatory cell infiltrations in liver tissues in the DMN-administered group were respectively increased about 17 times and about 5 times, after 4 weeks, in comparison with those of the normal control group. However, in the group administered with both the compound of the present invention (the compound of Example 21) and DMN, the damages to liver tissue and the inflammatory cell infiltrations in liver tissues were 276.0 cells/1000 cells and 85.33 cells/mm$^2$, respectively (i.e., ameliorated by about 50% and 55% in comparison with that of the DMN-administered group).

Figure 4:
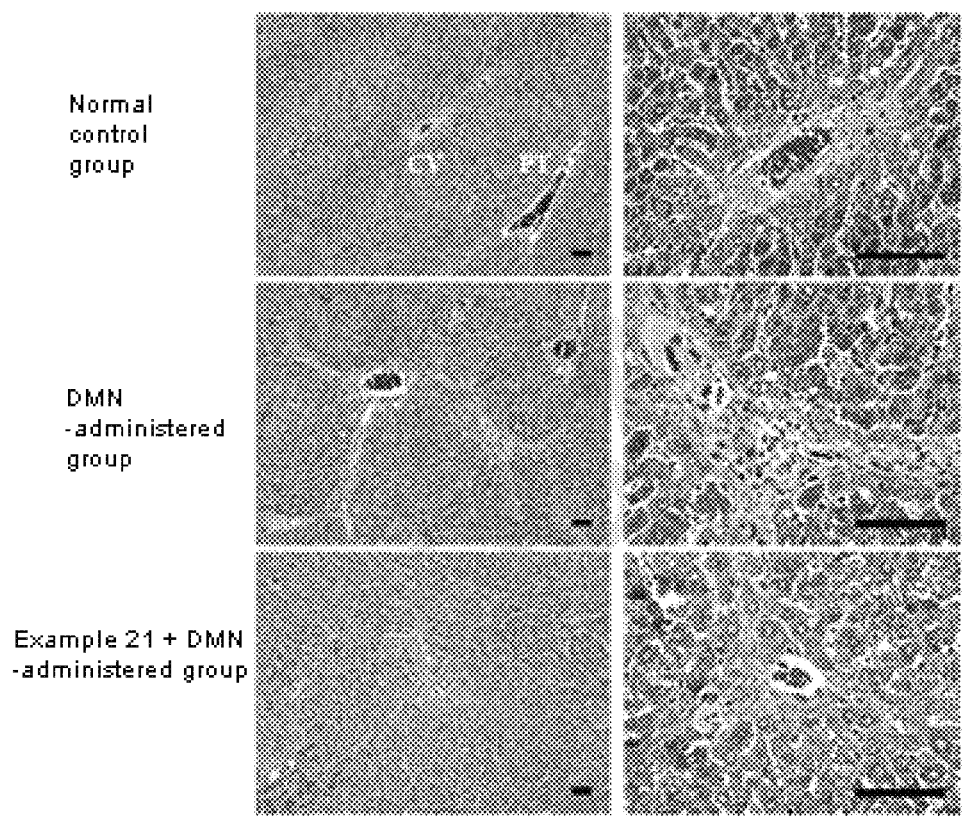
FIG. 4 show the results obtained by performing Masson's trichrome staining on the tissue specimens obtained in Test Example 3. Scale bar: left black line 100 μm, right black line 100 μm.

And also, as can be seen from the results of FIG. 4 and Table 7, the collagen fiber depositions in liver tissues in the DMN-administered group was increased about 12 times, after 4 weeks, in comparison with that of the normal control group. However, in the group administered with both the compound of the present invention (the compound of Example 21) and DMN, the collagen fiber depositions in liver tissues was 10.98%/mm$^2$ (i.e., reduced by about 62% in comparison with that of the DMN-administered group).

Therefore, it can be confirmed that the compounds of the present invention have an effectively-improving activity against the liver injuries including liver fibrosis.

The invention claimed is:

1. A compound of Formula 1 or pharmaceutically acceptable salt thereof:

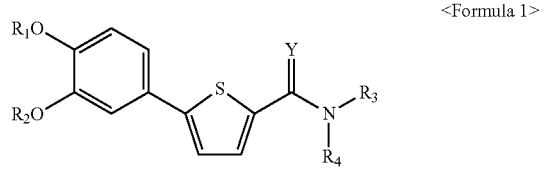

<Formula 1> wherein,
Y is O or S,
(1) when Y is O,
$R_1$ is hydrogen; or a $C_1$~$C_4$ alkyl group substituted with a mono- or di-$C_1$~$C_5$ alkylamino,
$R_2$ is a $C_1$~$C_6$ alkyl group,
$R_3$ is hydrogen, and
$R_4$ is a (4-(dimethylamino)tetrahydro-2H-pyran-4-yl) methyl group; a $C_1$~$C_4$ alkyl group substituted with a mono- or di-$C_1$~$C_5$ alkylamino; a $C_1$~$C_4$ alkyl group substituted with a nitrogen-containing cyclic ring (wherein the nitrogen-containing cyclic ring is morpholine, piperidine, or pyrrolidine which is optionally substituted with $C_1$~$C_4$ alkyl); or a piperidinyl group optionally substituted with $C_1$~$C_4$ alkyl,
(2) when Y is S,
$R_1$ and $R_2$ are, independently of each other, hydrogen; a $C_1$~$C_6$ alkyl group; or a $C_1$~$C_4$ alkyl group substituted with a mono- or di-$C_1$~$C_5$ alkylamino,
$R_3$ is hydrogen, and
$R_4$ is a $C_1$~$C_4$ alkyl group substituted with a mono- or di-$C_1$~$C_5$ alkylamino.

2. The compound or pharmaceutically acceptable salt thereof of claim 1, wherein
Y is O,
$R_1$ is hydrogen; or a diethylaminoethyl group, and
$R_2$ is a methyl group.

3. The compound or pharmaceutically acceptable salt thereof of claim 1, wherein
Y is O,
$R_1$ is hydrogen; or a diethylaminoethyl group,
$R_2$ is a methyl group,
$R_3$ is hydrogen, and
$R_4$ is a (4-(dimethylamino)tetrahydro-2H-pyran-4-yl) methyl group; a dimethylaminoethyl group; a diethylaminoethyl group; a diisopropylaminoethyl group; a morpholinoethyl group optionally substituted with $C_1$~$C_4$ alkyl; a piperidinoethyl group optionally substituted with $C_1$~$C_4$ alkyl; a pyrrolidinoethyl group optionally substituted with $C_1$~$C_4$ alkyl; or a piperidinyl group optionally substituted with $C_1$~$C_4$ alkyl.

4. The compound or pharmaceutically acceptable salt thereof of claim 1, wherein
Y is O,
$R_1$ is hydrogen; or a diethylaminoethyl group,
$R_2$ is a methyl group,
$R_3$ is hydrogen, and
$R_4$ is a (4-(dimethylamino)tetrahydro-2H-pyran-4-yl) methyl group.

5. The compound or pharmaceutically acceptable salt thereof of claim 1, wherein
Y is S,
$R_1$ is hydrogen; or a diethylaminoethyl group, and
$R_2$ is a methyl group.

6. The compound or pharmaceutically acceptable salt thereof of claim 1, wherein
Y is S,
$R_1$ is hydrogen; or a diethylaminoethyl group,
$R_2$ is a methyl group,
$R_3$ is hydrogen, and
$R_4$ is a diisopropylaminoethyl group.

7. A The compound or pharmaceutically acceptable salt thereof, which is one or more selected from the group consisting of:
N-(2-(diisopropylamino)ethyl)-5-(4-hydroxy-3-methoxyphenyl)thiophene-2-carboxamide hydrochloride;
N-(2-(diisopropylamino)ethyl)-5-(4-(2-diethylamino) ethoxy-3-methoxyphenyl)thiophene-2-carboxamide hydrochloride;
N-(2-(diisopropylamino)ethyl)-5-(4-hydroxy-3-methoxyphenyl)thiophene-2-thiocarboxamide hydrochloride;
N-(2-(diisopropylamino)ethyl)-5-(4-(2-diethylamino) ethoxy-3-methoxyphenyl)thiophene-2-thiocarboxamide hydrochloride;
N-isopropyl-5-(4-(2-diethylamino)ethoxy-3-methoxyphenyl)thiophene-2-carboxamide hydrochloride;
N-isopropyl-5-(4-(2-diethylamino)ethoxy-3-methoxyphenyl)thiophene-2-thiocarboxamide hydrochloride;
N-(2-(diethylamino)ethyl)-5-(4-hydroxy-3-methoxyphenyl)thiophene-2-carboxamide hydrochloride;
N-(2-(diethylamino)ethyl)-5-(4-(2-diethylamino)ethoxy-3-methoxyphenyl)thiophene-2-carboxamide hydrochloride;
N-(2-(dimethylamino)ethyl)-5-(4-hydroxy-3-methoxyphenyl)thiophene-2-carboxamide hydrochloride;

N-(2-(dimethylamino)ethyl)-5-(4-(2-diethylamino)ethoxy-3-methoxyphenyl)thiophene-2-carboxamide hydrochloride;

N-(2-(4-morpholino)ethyl)-5-(4-hydroxy-3-methoxyphenyl)thiophene-2-carboxamide hydrochloride;

N-(2-(1-piperidino)ethyl)-5-(4-hydroxy-3-methoxyphenyl)thiophene-2-carboxamide hydrochloride;

N-(2-(1-piperidino)ethyl)-5-(4-(2-diethylamino)ethoxy-3-methoxyphenyl)thiophene-2-carboxamide hydrochloride;

N-(2-(1-pyrrolidino)ethyl)-5-(4-hydroxy-3-methoxyphenyl)thiophene-2-carboxamide hydrochloride;

N-((4-(dimethylamino)tetrahydro-2H-pyran-4-yl)methyl)-5-(4-hydroxy-3-methoxyphenyl)thiophene-2-carboxamide hydrochloride;

N-((4-(dimethylamino)tetrahydro-2H-pyran-4-yl)methyl)-5-(4-(2-diethylamino)ethoxy-3-methoxyphenyl)thiophene-2-carboxamide hydrochloride;

N-(4-(1-methyl)piperidinyl)-5-(4-hydroxy-3-methoxyphenyl)thiophene-2-carboxamide hydrochloride;

N-(2-(2-(1-methyl)pyrrolidino)ethyl)-5-(4-hydroxy-3-methoxyphenyl)thiophene-2-carboxamide hydrochloride;

N-(2-(2-(1-methyl)pyrrolidino)ethyl)-5-(4-(2-diethylamino)ethoxy-3-methoxyphenyl)thiophene-2-carboxamide hydrochloride;

N—((S)-2-(1-ethyl)pyrrolidinomethyl)-5-(4-hydroxy-3-methoxyphenyl)thiophene-2-carboxamide hydrochloride; and N—((S)-2-(1-ethyl)pyrrolidinomethyl)-5-(4-(2-diethylamino)ethoxy-3-methoxyphenyl)thiophene-2-carboxamide hydrochloride.

8. N-((4-(dimethylamino)tetrahydro-2H-pyran-4-yl)methyl)-5-(4-hydroxy-3-methoxyphenyl)thiophene-2-carboxamide or pharmaceutically acceptable salt thereof.

9. N-((4-(dimethylamino)tetrahydro-2H-pyran-4-yl)methyl)-5-(4-(2-diethylamino)ethoxy-3-methoxyphenyl)thiophene-2-carboxamide or pharmaceutically acceptable salt thereof.

10. A pharmaceutical composition for inducing autophagy, comprising a therapeutically effective amount of the compound or pharmaceutically acceptable salt thereof according to claim 1 as an active ingredient.

11. The pharmaceutical composition of claim 10 for preventing, ameliorating or treating neurodegenerative diseases selected from the group consisting of Huntington's disease, Parkinson's disease, Alzheimer's disease, prion disease, multiple sclerosis, and Lou Gehrig's disease; hepatic diseases selected from the group consisting of liver fibrosis, liver cirrhosis, hepatitis, and fatty liver disease; metabolic diseases selected from the group consisting of diabetes, hyperlipidemia, obesity, and inflammation; or sepsis.

* * * * *